United States Patent
Suzuki et al.

(10) Patent No.: US 8,283,145 B2
(45) Date of Patent: Oct. 9, 2012

(54) CHONDROITIN-PRODUCING BACTERIUM AND METHOD OF PRODUCING CHONDROITIN

(75) Inventors: Kiyoshi Suzuki, Higashiyamato (JP); Kentaro Miyamoto, Higashiyamato (JP); Hiromi Kaseyama, Higashiyamato (JP)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 0 days.

(21) Appl. No.: 12/596,980

(22) PCT Filed: Apr. 24, 2008

(86) PCT No.: PCT/JP2008/058323
§ 371 (c)(1),
(2), (4) Date: Oct. 21, 2009

(87) PCT Pub. No.: WO2008/133350
PCT Pub. Date: Nov. 6, 2008

(65) Prior Publication Data
US 2010/0151532 A1    Jun. 17, 2010

Related U.S. Application Data

(60) Provisional application No. 60/913,713, filed on Apr. 24, 2007.

(51) Int. Cl.
C12P 19/04 (2006.01)
C12N 9/00 (2006.01)
C12N 1/20 (2006.01)
C12N 15/00 (2006.01)
C07H 21/04 (2006.01)

(52) U.S. Cl. ............ 435/183; 435/101; 435/252.3; 435/320.1; 536/23.2

(58) Field of Classification Search .......... None
See application file for complete search history.

(56) References Cited

U.S. PATENT DOCUMENTS

| | | |
|---|---|---|
| 6,372,466 B1 | 4/2002 | Habuchi et al. |
| 2006/0052335 A1 | 3/2006 | Narimatsu et al. |
| 2006/0057697 A1 | 3/2006 | Narimatsu et al. |
| 2008/0070996 A1 | 3/2008 | Narimatsu et al. |
| 2009/0155851 A1 | 6/2009 | Sugiura et al. |
| 2009/0263867 A1 | 10/2009 | Sugiura et al. |

FOREIGN PATENT DOCUMENTS

| | | |
|---|---|---|
| EP | 1 283 259 | 2/2003 |
| EP | 2 034 016 | 3/2009 |
| JP | 61-047701 | 3/1986 |
| WO | WO 01/80810 | 11/2001 |
| WO | WO 2007/023867 | 3/2007 |
| WO | WO 2007/069693 | 6/2007 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Witkowski et al. Biochemistry. Sep. 7, 1999; 38(36): 11643-50.*
Ninomiya, et al. "Molecular Cloning and Characterization of Chondroitin Polymerase from *Escherichia coli* Strain K4" *The Journal of Biological Chemistry*, vol. 277, No. 24, pp. 21567-21575, Jun. 14, 2002.
Lidholt, et al. "Biosynthesis of the *Escherichia coli* K4 Capsule Polysaccharide," *The Journal of Biological Chemistry*, vol. 272, No. 5, pp. 2682-2687, Jan. 31, 1997.
International Search Report issued to a related foreign application and dated Sep. 4, 2008.
DeAngelis, et al. "Identification and Molecular Cloning of a Chondroitin Synthase from *Pasteurella multocida* Type F," *The Journal of Biological Chemistry*, vol. 275, No. 31, pp. 24124-24129, Aug. 4, 2000.
Kitagawa, et al. "Molecular Cloning and Expression of a Novel Chondroitin 6-O-Sulfotransferase," *The Journal of Biological Chemistry*, vol. 275, No. 28, pp. 21075-21080, Jul. 14, 2000.

* cited by examiner

*Primary Examiner* — Christian Fronda
(74) *Attorney, Agent, or Firm* — Knobbe, Martens, Olson & Bear, LLP

(57) ABSTRACT

Chondroitin is produced by culturing a UDP-glucuronic acid-producing bacterium transfected with a kfoA gene derived from *Escherichia coli* K4 strain and a kfoC gene derived from *Escherichia coli* K4 strain and having chondroitin-producing ability. Chondroitin is collected from the bacterium.

6 Claims, 7 Drawing Sheets

(A)

(B)

(C)

(A)

(B)

(C)

(A)

(B)

(C)

(A)

(B)

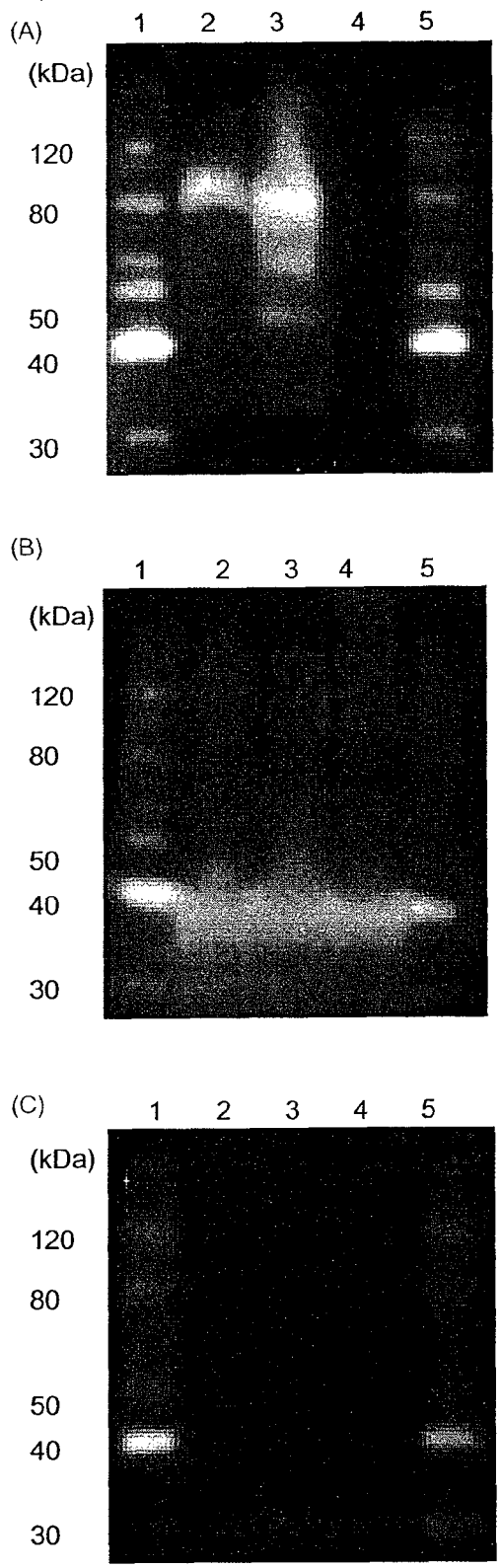

CHONDROITIN-PRODUCING BACTERIUM AND METHOD OF PRODUCING CHONDROITIN

CROSS-REFERENCE TO RELATED APPLICATIONS

This application is the U.S. National Phase under 35 U.S.C. § 371 of International Application PCT/JP2008/058323, filed Apr. 24, 2008, which claims priority to U.S. Provisional Application No. 60/913,713, filed Apr. 24, 2007.

TECHNICAL FIELD

The present invention relates to a chondroitin-producing bacterium and a method of producing chondroitin.

BACKGROUND ART

Chondroitin is a polysaccharide comprising a repeated structure of disaccharides of a glucuronic acid (GlcUA) residue and a N-acetyl-D-galactosamine (GalNAc) residue (-GlcUAβ(1-3)-GalNAcβ(1-4)-; in the present specification, also referred to as a chondroitin carbohydrate backbone). Chondroitin sulfate is a polysaccharide which consists by sulfation of chondroitin.

Conventionally, chondroitin and chondroitin sulfate are extracted and purified from cartilages, organs, and the like of animals. However, in recent years, a technique for artificially synthesizing a carbohydrate backbone common to chondroitin and chondroitin sulfate has been studied because of shortage of such materials as cartilages and organs.

Chondroitin synthases, which produce chondroitin by alternately transferring GlcUA and GalNAc from their donor substrates to acceptor oligosaccharides, have been reported, and a method of producing chondroitin using the enzyme has been proposed.

J. Biol. Chem. 275(31), 24124-24129 (2000) discloses a chondroitin synthase derived from *Pasteurella multocida*.

In addition, WO 2003/102193 and WO 2003/102194 disclose chondroitin synthases derived from human.

Moreover, U.S. 2003-0109693 (JP 2003-199583 A) discloses a novel chondroitin synthase (KfoC) produced by *Escherichia coli* K4 strain.

However, in the case of producing chondroitin by the enzymatic methods, it is necessary to prepare expensive materials such as oligosaccharides as acceptors and sugar nucleotides for donors of GlcUA and GalNAc, and thus a method of producing chondroitin using more inexpensive materials has been desired.

*Escherichia coli* K4 strain is known to produce a polysaccharide having a chondroitin backbone structure as a capsule. However, its structure consists of a repeating unit comprising trisaccharides of a GalNAc residue, a GlcUA residue and a fructose residue that is bound to a C3-hydroxyl group of a GlcUA residue. In addition, over 100 chemically different capsular polysaccharides have been detected in *Escherichia coli*. For example, *Escherichia coli* K5 strain produces a capsule polysaccharide K5 which has a carbohydrate backbone of heparin/heparan sulfate (J. Biol. Chem., 272(5), p 2682-2687, 1997). However, the existence of *Escherichia coli* which produces chondroitin itself has not been known. Therefore, a method of producing chondroitin using an *Escherichia* bacterium is unknown.

Although US Published Patent Application 2007-0281342 discloses a method of producing chondroitin by using a recombinant gram-positive *Bacillus* bacterium introduced with a chondroitin synthase gene derived from *Pasteurella multocida*, further development in fermentative production of chondroitin has been desired.

DISCLOSURE OF THE INVENTION

An object of the present invention is to provide a novel microorganism capable of producing chondroitin and a novel method of producing chondroitin using the microorganism.

The inventors of the present invention have made extensive studies, and as a result, have discovered that a UDP-glucuronic acid-producing bacterium such as *Escherichia coli* K5 strain which is introduced with kfoA and kfoC genes derived from *Escherichia coli* K4 strain produces chondroitin at high efficiency, thus completed the present invention.

An object of the present invention is to provide a UDP-glucuronic acid-producing bacterium, which is introduced with a kfoA gene derived from *Escherichia coli* K4 strain and a kfoC gene derived from *Escherichia coli* K4 strain and has chondroitin-producing ability.

Here, the kfoA gene derived from *Escherichia coli* K4 strain is preferably a gene encoding a protein selected from the group consisting of the following (A) and (B):

(A) a protein comprising the amino acid sequence of SEQ ID NO: 2; and (B) a protein comprising an amino acid sequence of SEQ ID NO: 2 including substitution, deletion, insertion, or addition of one or several amino acids and having UDP-glucose-4-epimerase activity.

The kfoA gene derived from *Escherichia coli* K4 strain is preferably a DNA selected from the group consisting of the following (a) and (b):

(a) a DNA comprising the nucleotide sequence of SEQ ID NO: 1; and (b) a DNA that hybridizes with a DNA comprising the nucleotide sequence complementary to SEQ ID NO: 1 under stringent conditions and encodes a protein comprising UDP-glucose-4-epimerase activity.

In addition, the kfoC gene derived from *Escherichia coli* K4 strain is preferably a gene encoding a protein selected from the group consisting of the following (C) and (D):

(C) a protein comprising the amino acid sequence of SEQ ID NO: 4; and (D) a protein comprising an amino acid sequence of SEQ ID NO: 4 including substitution, deletion, insertion, or addition of one or several amino acids and having chondroitin synthase activity.

In addition, the kfoC gene derived from *Escherichia coli* K4 strain is preferably a DNA selected from the group consisting of the following (c) and (d):

(c) a DNA comprising the nucleotide sequence of SEQ ID NO: 3; and (d) a DNA that hybridizes with a DNA comprising the nucleotide sequence complementary to SEQ ID NO: 3 under stringent conditions and encodes a protein having chondroitin synthase activity.

In addition, the kfoC gene derived from *Escherichia coli* K4 strain is preferably a gene encoding a protein selected from the group consisting of the following (E) and (F):

(E) a protein comprising the amino acid sequence of SEQ ID NO: 6; and (F) a protein comprising an amino acid sequence of SEQ ID NO: 6 including substitution, deletion, insertion, or addition of one or several amino acids and having chondroitin synthase activity.

In addition, the kfoC gene derived from *Escherichia coli* K4 strain is preferably a DNA selected from the group consisting of the following (e) and (f):

(e) a DNA comprising the nucleotide sequence of SEQ ID NO: 5*l*; and (f) a DNA that hybridizes with a DNA comprising the nucleotide sequence complementary to SEQ ID NO: 5 under stringent conditions and encodes a protein having chondroitin synthase activity.

The UDP-glucronic acid-producing bacterium is preferably *Escherichia coli* K5 strain.

Another object of the present invention is to provide a method of producing chondroitin comprising at least the following steps (1) and (2):

(1) culturing the bacterium as described above; and (2) collecting chondroitin from the culture.

Another object of the present invention is to provide a method of producing chondroitin sulfate comprising: producing chondroitin by the method as described above; and then sulfating the chondroitin to yield chondroitin sulfate.

Another object of the present invention is to provide a vector comprising a kfoA gene derived from *Escherichia coli* K4 strain and a kfoC gene derived from *Escherichia coli* K4 strain.

BRIEF DESCRIPTION OF THE DRAWINGS

FIG. 7 is a drawing (photograph) showing expression of KfoA, KfoC and Kfo∆C proteins using (A) an anti-KfoC antibodies (EK-C) as 1$^{st}$ antibody, (B) an anti-KfoA antibodies (EK-A) as 1$^{st}$ antibody and (C) normal rabbit serum. Lane 1 and 5 show molecular marker, MagicMarkXP standard (Invitrogen), Lane 2 shows a strain introduced with pTrcHis-kfoCA, Lane 3 shows a strain introduced with pTrcHis-kfo ∆CA and Lane 4 shows a strain introduced with pTrcHis-kfoA.

DESCRIPTION OF THE PREFERRED EMBODIMENTS

Figure 1:
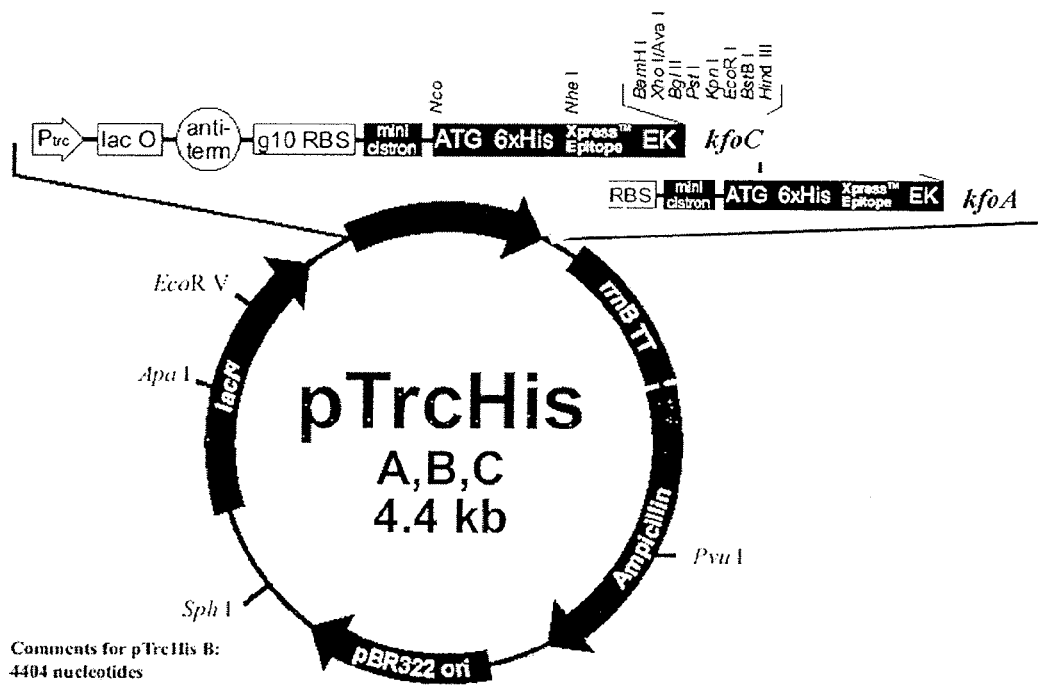
FIG. 1 is a drawing showing a structure of a vector for expressing kfoA and kfoC genes.

Hereinafter, the present invention will be described in detail.

<1> Bacterium of the Present Invention

The bacterium of the present invention is a UDP-glucuronic acid-producing bacterium introduced with kfoA and kfoC genes derived from *Escherichia coli* K4 strain and having chondroitin-producing ability.

The "UDP-glucuronic acid-producing bacterium" provides UDP-glucuronic acid, which is used for production of polysaccharide composed of glucuronic acid. The "UDP-glucuronic acid-producing bacterium" is not limited as long as it produces UDP-glucuronic acid, and examples thereof include a bacterium belonging to the genus *Gluconacetobacter* such as *Gluconacetobacter hansenii* and *Gluconacetobacter xylinus*, a bacterium belonging to the genus *Rhizobium* such as *Rhizobium meffloti*, a bacterium belonging to the genus *Acetobacter* such as *Acetobacter xylinum*, a bacterium belonging to the genus *Erwinia* such as *Erwinia amylovora*, a bacterium belonging to the genus *Thiobacillus* such as *Thiobacillus ferrooxidans*, a bacterium belonging to the genus *Xylella* such as *Xylella fastidiosa*, a bacterium belonging to the genus *Sinorhizobium* such as *Sinorhizobium meliloti*, a bacterium belonging to the genus *Rhodococcus* such as *Rhodococcus rhodochrous*, a bacterium belonging to the genus *Klebsiella* such as *Klebsiella aerogenes*, a bacterium belonging to the genus *Enterobacter* such as *Enterobacter aerogenes*, and a bacterium belonging to the genus *Escherichia* such as *Escherichia coli*.

The "UDP-glucuronic acid-producing bacterium" is preferably a bacterium belonging to the genus *Escherichia* and capable of producing UDP-glucuronic acid, and more preferably a bacterium belonging to *Escherichia coli* and capable of producing UDP-glucuronic acid.

A specific example thereof includes *Escherichia coli* K5 strain. The K5 strain has been deposited at the American Type Culture Collection (ATCC: P.O. Box 1549, Manassas, Va. 20108, United States of America) under the accession number of ATCC23506 and is available from the catalogue or homepage of ATCC.

The strain to be introduced with the kfoA and kfoC genes may be a strain which is a derivative of the *Escherichia coli* K5 strain, and such derivative strains may be obtained by introducing a gene mutation into the *Escherichia coli* K5 strain or introducing a gene into the *Escherichia coli* K5 strain by genetic recombination. That is, one aspect of the bacterium of the present invention includes: a strain obtained by introducing kfoA and kfoC genes derived from *Escherichia coli* K4 strain into *Escherichia coli* K5 strain; a strain obtained by introducing kfoA and kfoC genes derived from *Escherichia coli* K4 strain into *Escherichia coli* K5 strain and further introducing a gene mutation; and a strain obtained by introducing kfoA and kfoC genes derived from *Escherichia coli* K4 strain into *Escherichia coli* K5 strain and further introducing another gene.

Examples of the kfoA gene derived from *Escherichia coli* K4 strain include a DNA encoding a protein comprising the amino acid sequence of SEQ ID NO: 2 and a DNA comprising the nucleotide sequence of SEQ ID NO: 1.

In general, substitution, deletion, insertion, or addition in one or several amino acids that constitute a protein has no effect on the activity of the protein, in many cases, and therefore, the kfoA gene derived from *Escherichia coli* K4 strain may be a gene encoding a protein comprising an amino acid sequence of SEQ ID NO: 2 including substitution, deletion, insertion, or addition of one or several amino acids and having UDP-glucose-4-epimerase activity.

The phrase "one or several amino acids" as used herein refers to the number of amino acids that may cause a substitution, deletion, insertion, or addition without impairing UDP-glucose 4-epimerase activity. Specifically, the number is, for example, an integer of 1 to 20, preferably an integer of 1 to 10, more preferably an integer of 1 to 5.

Meanwhile, the kfoA gene derived from *Escherichia coli* K4 strain may be a gene encoding a protein comprising an amino acid sequence that is not less than 90% identical, preferably not less than 95% identical, more preferably not less than 98% identical to the entire sequence of SEQ ID NO: 2, and having UDP-glucose 4-epimerase activity.

The kfoA gene derived from *Escherichia coli* K4 strain may be obtained by PCR using a chromosomal DNA of *Escherichia coli* K4 strain as a template.

*Escherichia coli* K4 strain has been deposited at the American Type Culture Collection (ATCC) under the accession number of ATCC23502 and is available from the catalogue or homepage of ATCC.

The gene encoding a protein comprising an amino acid sequence of SEQ ID NO: 2 including substitution, deletion, insertion, or addition of one or several amino acids or an amino acid sequence that is not less than 90% identical to the entire sequence of SEQ ID NO: 2 and having UDP-glucose-4-epimerase activity may be obtained by modifying the nucleotide sequence of SEQ ID NO: 1 so that substitution, deletion, insertion, or addition of one or several amino acids is introduced into the amino acid sequence of SEQ ID NO: 2 by site-specific mutagenesis (Kramer, W. and Frits, H. J., Meth. in Enzymol., 154, 350(1987); Kunkel, T. A. et al., Meth. in Enzymol., 154, 367(1987)) or the like.

The gene may also be obtained by: screening a DNA encoding a protein having UDP-glucose 4-epimerase activity by hybridization with a DNA comprising the nucleotide sequence complementary to the nucleotide sequence of SEQ ID NO: 1 or a partial sequence thereof under stringent conditions.

The term "stringent conditions" refers to conditions under which so-called specific hybrid is formed and non-specific hybrid is not formed (see Sambrook, J. et al., Molecular Cloning A Laboratory Manual, second Edition, Cold Spring Harbor Laboratory Press (1989), etc.). Specific examples of the "stringent conditions" include conditions for hybridization at 42° C. in a solution containing 50% formamide, 4×SSC, 50 mM HEPES (pH 7.0), 10× Denhardt's solution, 100 μg/ml salmon sperm DNA and washing with 2×SSC, 0.1% SDS solution at room temperature and then 0.1×SSC, 0.1% SDS solution at 60° C.

Whether the gene obtained as described above encodes a protein having UDP-glucose 4-epimerase activity can be judged by introducing the resultant gene into an appropriate host to express the protein and then measuring the UDP-glucose 4-epimerase activity in accordance with the method described in J. Biol. Chem., 277(24), p 21567-21575, 2002.

Examples of the kfoC gene derived from *Escherichia coli* K4 strain include a DNA encoding a protein comprising the amino acid sequence of SEQ ID NO: 4 and a DNA comprising the nucleotide sequence of SEQ ID NO: 3. Examples of the kfoC gene derived from *Escherichia coli* K4 strain also include a DNA encoding a protein comprising the amino acid sequence of SEQ ID NO: 6 and a DNA comprising the nucleotide sequence of SEQ ID NO: 5.

The kfoC gene derived from *Escherichia coli* K4 strain may be a gene encoding a protein comprising an amino acid sequence of SEQ ID NO: 4 or 6 including substitution, deletion, insertion, or addition of one or several amino acids and having chondroitin synthase activity.

The kfoC gene derived from *Escherichia coli* K4 strain may be a gene encoding a protein comprising an amino acid sequence that is not less than 90% identical, preferably not less than 95% identical, more preferably not less than 98% identical to the entire sequence of SEQ ID NO: 4 or 6 and having chondroitin synthase activity.

The term "chondroitin synthase activity" as used herein refers to an activity to alternately transfer GlcUA from a GlcUA donor or GalNAc from a GalNAc donor to the non-reduced end of a sugar chain.

The kfoC gene derived from *Escherichia coli* K4 strain may be obtained by PCR using a chromosomal DNA of *Escherichia coli* K4 strain as a template. Furthermore, the kfoC gene encoding the amino acid sequence of SEQ ID NO: 6 such as a DNA comprising the nucleotide sequence of SEQ ID NO: 5 may be obtained according to the method described in WO2007/145197.

The gene encoding a protein comprising an amino acid sequence of SEQ ID NO: 4 or 6 including substitution, deletion, insertion, or addition of one or several amino acids or an amino acid sequence that is not less than 90% identical to the entire sequence of SEQ ID NO: 4 or 6 and having chondroitin synthase activity may be obtained by modifying the nucleotide sequence of SEQ ID NO: 3 or 5 so that substitution, deletion, insertion, or addition of one or several amino acids is introduced into the amino acid sequence of SEQ ID NO: 4 or 6 by site-specific mutagenesis or the like.

The gene may also be obtained by: screening a DNA encoding a protein having chondroitin synthase activity by hybridization with a DNA comprising the nucleotide sequence complementary to the nucleotide sequence of SEQ ID NO: 3 or 5 or a partial sequence thereof under stringent conditions.

The definitions of the terms "one or several" and "stringent conditions" are the same as described above.

Whether the gene obtained as described above encodes a protein having chondroitin synthase activity can be judged by introducing the resultant gene into an appropriate host to express the protein and then measuring the chondroitin synthase activity in accordance with the method described in U.S. 2003-0109693 (JP 2003-199583 A).

The bacterium of the present invention can be obtained by introducing a kfoA gene derived from *Escherichia coli* K4 strain and a kfoC gene derived from *Escherichia coli* K4 strain into a UDP-glucuronic acid-producing bacterium as described above.

The term "introduction" used in the present invention includes introduction of both of the genes into a UDP-glucuronic acid-producing bacterium using a vector such as a plasmid or a bacteriophage and introduction of both of the genes on a chromosome of the UDP-glucuronic acid-producing bacterium by homologous recombination or the like.

The vector such as a plasmid or a bacteriophage to be used herein is not particularly limited as long as they can be used for gene introduction into *Escherichia coli*, and examples thereof include pTrcHis (Invitrogen Corporation), pET vector (Novagen), and pGEX vector (Amersham Pharmacia).

In introduction of a kfoA gene derived from *Escherichia coli* K4 strain and a kfoC gene derived from *Escherichia coli* K4 strain, native promoters of the genes may be used, but it is preferable to use a promoter that is potent in *Escherichia coli*, such as lac promoter, trp promoter, trc promoter, PR promoter, or lacUV promoter.

The kfoA gene and kfoC gene derived from *Escherichia coli* K4 strain may be introduced one by one or simultaneously introduced using a single vector. It is more preferable to use a vector such as a plasmid or a bacteriophage carrying both of the kfoA and kfoC genes because introduction and expression of the genes can be easily performed.

The kfoA and kfoC genes derived form *Escherichia coli* K4 strain may be introduced so that they are expressed as fusion proteins with other peptides.

Examples of the other peptides include polyhistidine tag and GST (glutathione-S-transferase) tag. Expression of the gene products as fusion proteins is preferable because detection (confirmation of expression) of the gene products can be easily performed.

Introduction of a gene may be performed by a known transformation method. Examples of the method include the electroporation method, the DEAE-dextran method, and the calcium phosphate method.

Introduction of a gene can be confirmed by: a method of detecting a gene, such as RT-PCR or Northern blotting; a method of peculiarly detecting expression of a recombinant protein, such as Western blotting; and an activity measurement method as described above.

If the kfoA gene derived from *Escherichia coli* K4 strain and the kfoC gene derived from *Escherichia coli* K4 strain introduced work in a UDP-glucuronic acid-producing bacterium, the bacterium acquires the ability to produce chondroitin as a capsular polysaccharide.

<2> Method of Producing Chondroitin

The method of producing chondroitin of the present invention comprises at least the following steps (1) and (2).
(1) culturing a bacterium of the present invention.
(2) collecting chondroitin from the culture.

The culture may be performed by a general method for culturing bacteria belonging to the genus *Escherichia*.

The culture medium is not particularly limited as long as it can be used for culture of bacteria belonging to the genus *Escherichia*, and preferable examples thereof include LB medium (Luria-Bertani medium) (containing 10.0 g of Bacto-tryptone, 5.0 g of Bacto-yeast extract, and 5.0 g of NaCl per liter) and CYG medium (2.0% casamino acid, 0.5% yeast extract, and 0.2% glucose, adjust pH to 7.0 before autoclaving). In the case where a gene is introduced using a vector containing an antibiotics-resistant gene, the medium preferably contains an antibiotics corresponding to the gene.

Culture conditions are not particularly limited as long as bacteria belonging to the genus *Escherichia can* grow, and in order to produce chondroitin at high efficiency, culture is preferably performed at 20 to 40° C. for 8 to 72 hours.

In order to produce chondroitin at high efficiency, a bacterium may be precultured in a plate or liquid medium.

The method of collecting chondroitin from culture is not particularly limited as long as chondroitin can be collected, and examples thereof include the method as described in the Examples shown below. Specifically, harvested recombinant cells are suspended into PBS (phosphate-buffered saline) or the like; treating the cells with lysozyme, DNaseI, and proteinase K; and removing proteins. Chondroitin can be detected by, for example, treating the fraction with chondroitinase and performing a disaccharide composition analysis.

<3> Method of Producing Chondroitin Sulfate

Chondroitin sulfate can be produced by further sulfating chondroitin prepared from the recombinant bacteria disclosed in this invention.

The sulfation may be performed by a known method of sulfating glycosaminoglycan, which is not particularly limited, and examples thereof include the method described in JP 61-47701 A.

In addition, the sulfation may be performed using an enzyme for transferring a sulfate group to chondroitin (sulfotransferase). Under existence of 3'-phosphoadenosine 5'-phosphosulfate (PAPS) as a sulfate donor, sulfotransferases can produce chondroitin sulfate by reacting to chondroitin produced by the recombinant bacteria disclosed in this invention. Examples of a known sulfotransferase for transferring a sulfate group to chondroitin include chondroitin 6-O-sulfate group transferase (J. Biol. Chem., 275 (28), 21075-21080 (2000)) and galactosaminoglycan 4-sulfate group transferase (JP 2000-4877 A).

EXAMPLES

Hereinafter, the present invention will be described in detail by referring to the examples.

Example 1

Preparation of KfoC/KfoA Co-Expression Vector

<Amplification of kfoA Gene>

PCR was performed using a chromosomal DNA of *E. coli* K4 strain as a template according to the method described in J. Biol. Chem., Vol. 277, Issue 24, 21567-21575, and the resultant PCR product was inserted into pTrcHis (histidine fusion protein expression vector, Invitrogen), to thereby yield pTrcHis-kfoA.

Primers used are as follows:

```
K4A-SP:
5'-CGGGATCCCGATGAGTATTCTTAATCAAGC-3' (SEQ ID NO: 7)
and

K4A-AS:
5'-GGAATTCCGGCCAGTCTACATGTTTATCAC-3' (SEQ ID NO: 8)
```

<Amplification of kfoC Gene>

PCR was performed using a chromosomal DNA of *E. coli* K4 strain as a template according to the method described in JP 2003-199583 A, and the resultant PCR product was inserted into pTrcHis, to thereby yield pTrcHis-kfoC.

Primers used are as follows:

```
                                           (SEQ ID NO: 9)
K4C-SP:    5'-CGGGATCCCGATGAGTATTCTTAATCAAGC-3'
and (SEQ ID NO: 10)
K4C-AS:    5'-GGAATTCCGGCCAGTCTACATGTTTATCAC-3'.
```

<Preparation of pTrcHis-kfoCA> pTrcHis-kfoCA was prepared from the above-mentioned pTrcHis-kfoA and pTrcHis-kfoC as follows.

First, the NotI-SalI site was introduced into the C-terminal sequence of pTrcHis-kfoC by PCR. PCR was performed using the primers shown below to amplify the full length of pTrcHis-kfoC from the C-terminal side of kfoC, and the resultant PCR product was self-ligated, to thereby yield a plasmid pTrcHis-kfoC-NotI-SalI.

Primers used are as follows:

```
                                           (SEQ ID NO: 11)
    NotSal-pTrcHisC-rev:
    5'-GCGGCCGCAAAACAGCCAAGCTTCGAATTC-3'
    and
```

-continued (SEQ ID NO: 12)
NotSal-pTrcHisC-for:
5'-ACGCGTCGACGGCGGATGAGAGAAGATTTTCA-3'

Then, Primers (NotI-RBS-KfoA-N: 5'-GCGGCCG-CAAAATTAAAGAGGTATATATTAATGTATCGA-3' (SEQ ID NO: 13) and SalI-KfoA-C: 5'-GTCGACCTCTCATC-CGCCAAAACA-3' (SEQ ID NO: 14)) were designed at the upstream of the ribosome binding site (RBS) and the C-terminal region of kfoA of pTrcHis-kfoA, respectively and used for PCR using pTrcHis-kfoA as a template. Then, the resultant PCR product was inserted into pCR4-TOPO (Invitrogen), to thereby yield pCR4-TOPO-kfoA.

An insert containing kfoA was excised from pCR4-TOPO-kfoA with NotI-SalI and introduced into the NotI-SalI site of pTrcHis-kfoC-NotI-SalI, and the resultant plasmid was named pTrcHis-kfoCA (FIG. 1).

Example 2

Co-Expression of the Recombinant KfoC and KfoA

The expression vector, pTrcHis-kfoCA, was introduced into *Escherichia coli* K5 strain by electroporation (cell 100 μL, 200 Ω, 25 μF, 2.5 kV, cuvette 0.1 cm), to thereby yield *E. coli* K5/pTrcHis-kfoCA strain. Colonies were transferred into LB medium supplemented with 100 ppm ampicillin, and then the seed culture was incubated at 37° C. overnight. One mL of the seed culture was transferred to 20 mL of CYG medium supplemented with 100 ppm ampicillin. The recombinant bacteria were cultured at 37° C. for 3 hours (OD600=1.8, 1.7-2.0), and then to the culture was added IPTG at a final concentration of 1.0 mM. The resulting culture was cultivated at 37° C. for further 5 hours to induce expression of the recombinant proteins.

Figure 2:
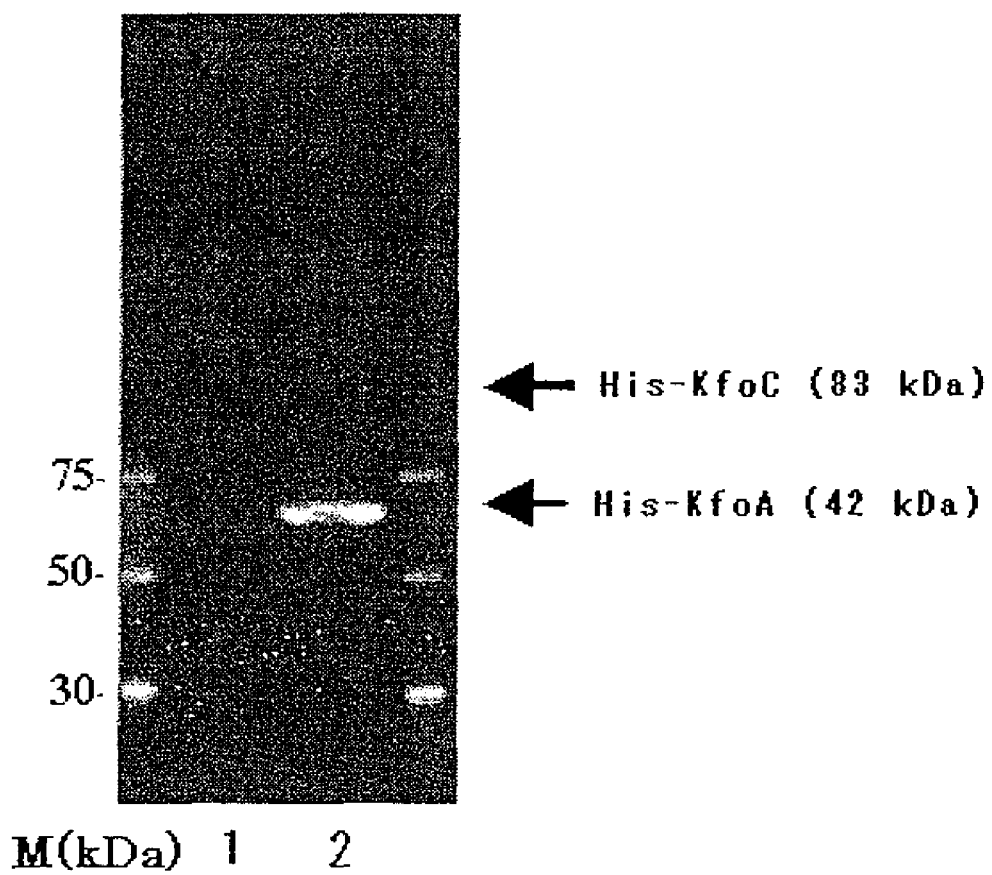
FIG. 2 is a drawing (photograph) showing expression of KfoA and KfoC proteins. Lane 1 shows a strain introduced with no plasmid (control), Lane 2 shows a strain introduced with pTrcHis-kfoCA, and M shows a molecular weight marker.

Bacterial cells were harvested from 900 μL of the culture by centrifugation. The obtained cells were suspended in 90 μL of Laemmli buffer (×1). After heating in a boiling water bath for 10 min, 10 μL of the supernatant was subjected to SDS-PAGE in a 5/20% gradient gel and transferred to a PVDF membrane, followed by Western analysis to detect expression of recombinant proteins. Anti-Penta-His-HRP (QIAGEN) diluted to 1/2,000 was used for detection of recombinant histidine fusion proteins. As a result, expressions of the recombinant proteins KfoA and KfoC were confirmed (FIG. 2).

Example 3

Preparation of Polysaccharide and its Detection by Disaccharide Analysis
<Preparation of Bacterial Cells>
*E. coli* K5/pTrcHis-kfoCA strain was cultured in LB medium supplemented with 100 ppm ampicillin as a seed culture. The seed culture (750 μL) was transferred into CYG medium supplemented with 100 ppm ampicillin (15 mL), and then it was cultured at 37° C. for 3 hours. To the culture was added IPTG (final concentration: 1 mM), and cultivation was further performed for 5 hours.

The bacterial cells were harvested by centrifugation.
<Preparation of Culture Supernatant>
The seed culture (1 mL) was transferred into CYG medium supplemented with 100 ppm ampicillin (20 mL), and then it was cultured at 37° C. for 3 hours. To the culture was added IPTG (final concentration: 0.1 mM), and cultivation was further performed for 5 hours. The culture supernatant was harvested by centrifugation.

<Preparation of Polysaccharide Fraction>
Polysaccharides were prepared from the recombinant cells and culture supernatant by the following three methods.

Preparation 1) The obtained bacterial described above were resuspended in PBS and treated with lysozyme and DNaseI at 37° C. for 1 hour, followed by treatment with proteinase K at 37° C. for 1 hour. Then, the enzymes were subjected to heat inactivation, and proteins were removed by precipitation with 70% ammonium sulfate. The resulting supernatant fraction was dialyzed against 10 mM Tris-HCl (pH 8.0) to yield Sample L.

Preparation 2) The obtained bacterial described above were treated with the agents for purifying plasmid: P1 (containing lysozyme), P2, and P3 (QIAGEN) sequentially, according to the manufacturer's instructions. After harvesting by centrifugation, the supernatant was subjected to ethanol precipitation. The precipitates were harvested by centrifugation and resuspended in 100 μL of sterilized water. The suspension was treated with DNaseI at 37° C. for 1 hour to digest DNAs, followed by treatment with proteinase K at 37° C. for 1 hour. Then, the enzymes were subjected to heat inactivation, and proteins were removed by precipitation with 70% ammonium sulfate. The resulting supernatant fraction was dialyzed against 10 mM Tris-HCl (pH 8.0) to yield Sample E.

Preparation 3) The culture supernatant (20 mL) was evaporated to dryness. The dried materials were dissolved into 2 ml of distilled water. The solution was dialyzed against 10 mM Tris-HCl (pH 8.0) to yield Sample S.
<Detection of Chondroitin by Disaccharide Analysis>
Samples L, E and S (100 μL each) were treated with cABC (chondroitinase ABC; manufactured by Seikagaku Corporation) in 50 mM Tris-HCl buffer (pH 8.0) containing 50 mM NaOAc at 37° C. overnight.

Figure 3:
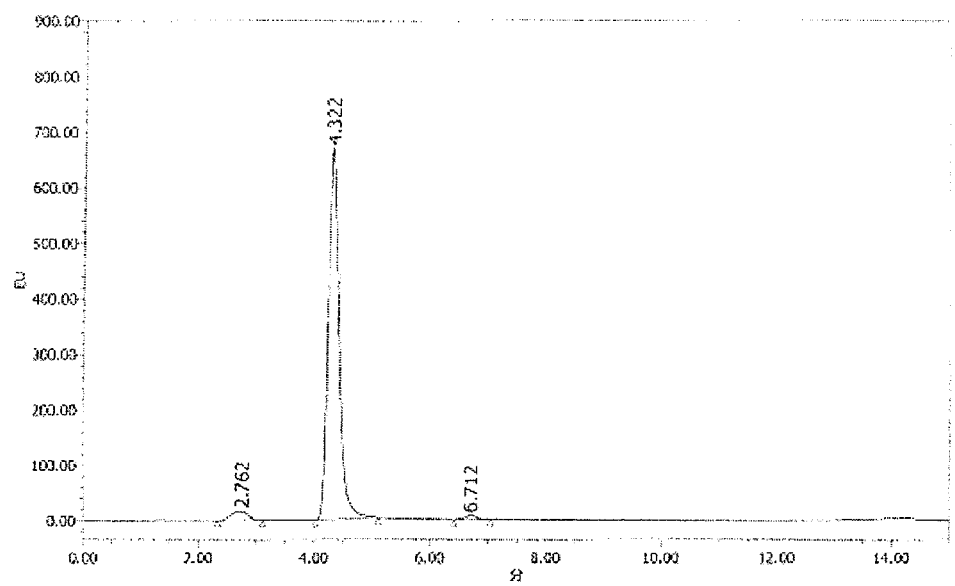
FIG. 3 shows the results of disaccharide composition analyses using fluorescent HPLC system for the fraction L treated with chondroitinase ABC (cABC) (A), the fraction L treated with no cABC (B), and the fraction L treated with heat-inactivated cABC (C).
Figure 3:
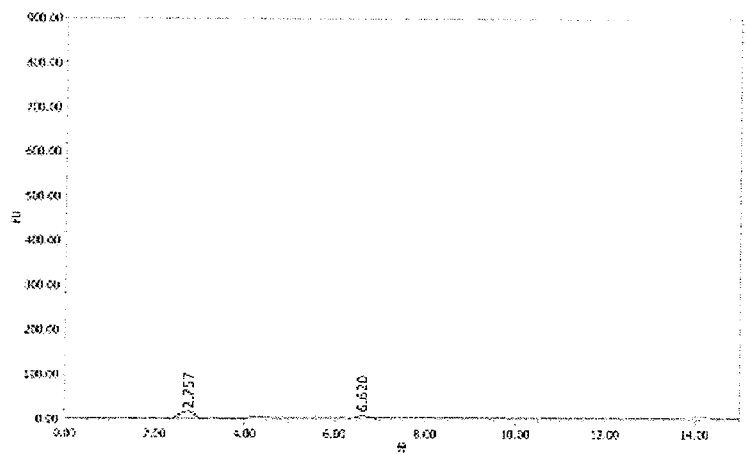
Figure 3:
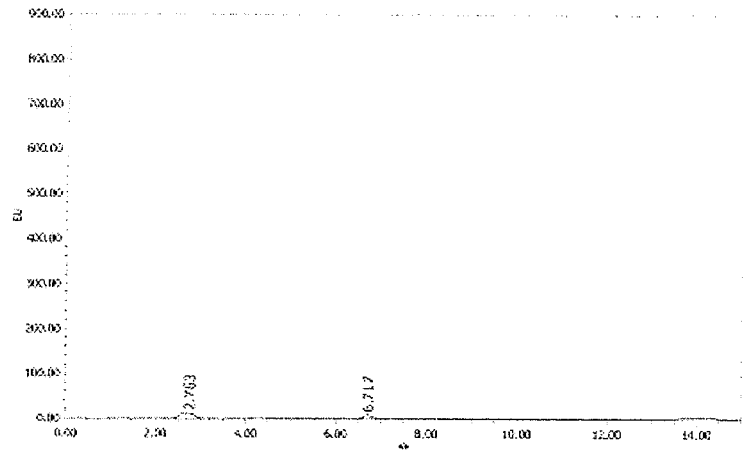
Figure 4:
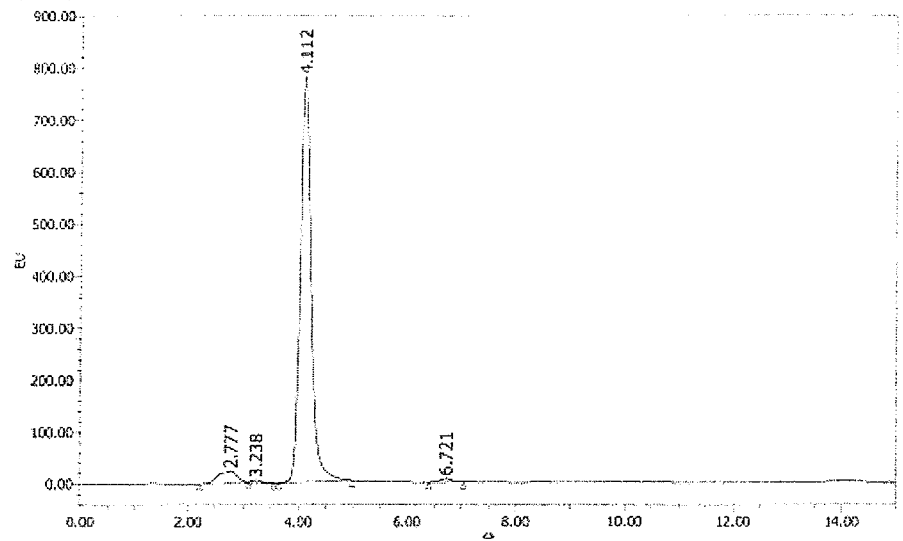
FIG. 4 shows results of fluorescence disaccharide analyses for the fraction E treated with cABC (A), the fraction E treated with no cABC (B), and the fraction E treated with heat-inactivated cABC (C).
Figure 4:
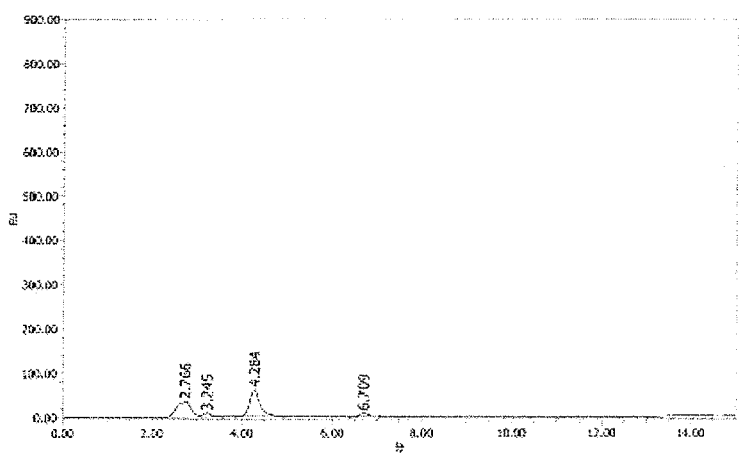
Figure 4:
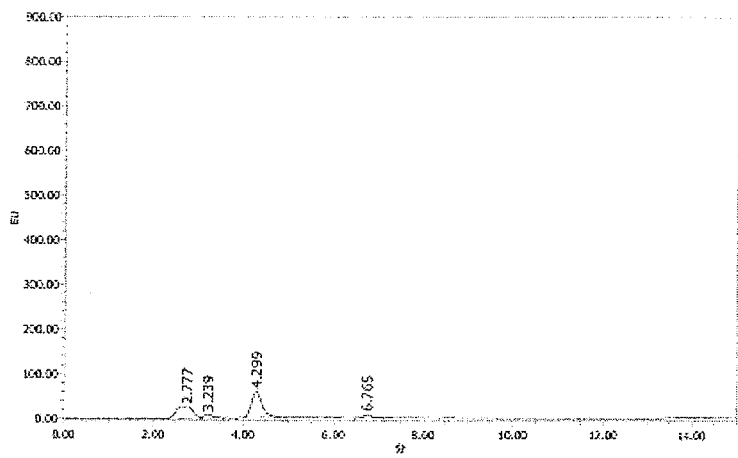
Figure 5:
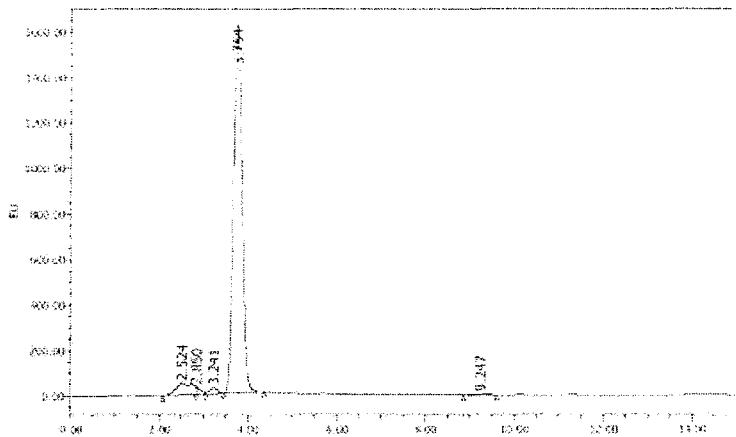
FIG. 5 shows results of fluorescence disaccharide analyses for the fraction S treated with cABC (A), the fraction S treated with no cABC (B), and the fraction S treated with heat-inactivated cABC (C).
Figure 5:
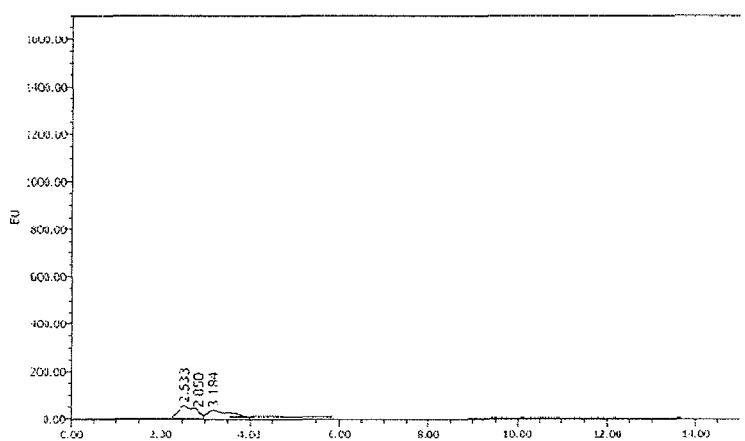
Figure 5:
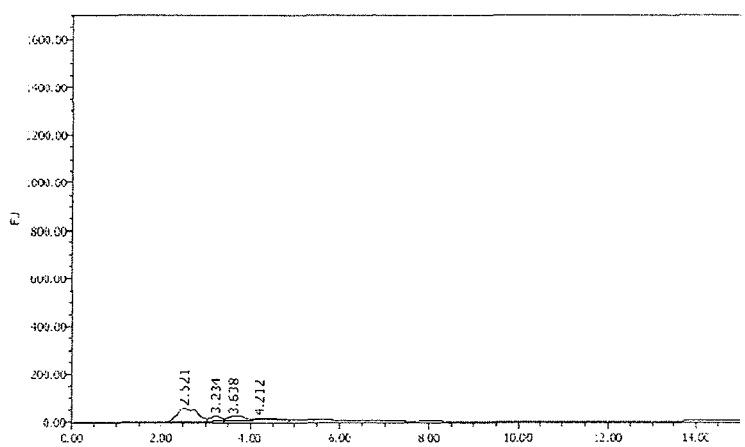

As controls, Samples L, E and S treated with no cABC and Samples L, E and S treated with heat-inactivated cABC were prepared. Ultrafiltration was performed to remove macromolecules with sizes equal to or more than 10,000, and the samples were analyzed by disaccharide composition analysis using a fluorescent HPLC system (J Biol Chem. 2000 Jul. 21;275(29):2269-2275.) (FIGS. 3, 4 and 5). Senshu Pak Decosil C22 (4.6 I.D.×150 mm) was used as a separation column in the HPLC system, and excitation and emission wavelength of the fluorescence detector were set to 346 nm and 410 nm, respectively.

Figure 6:
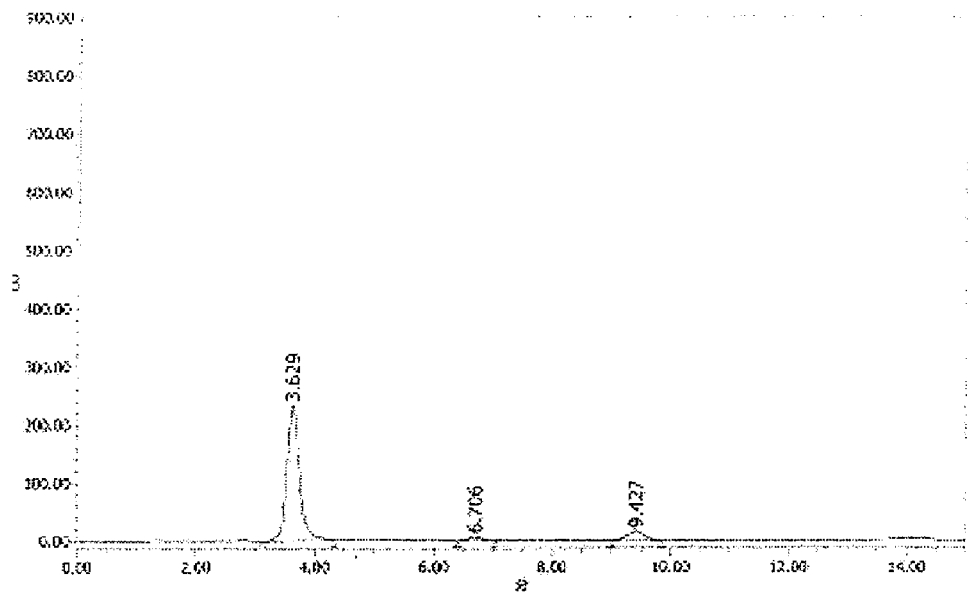
FIG. 6 shows results of fluorescence disaccharide analyses for the chondroitin standard treated with cABC (A) and a mixture of the chondroitin standard treated with cABC and the fraction L treated with cABC (B).
Figure 6:
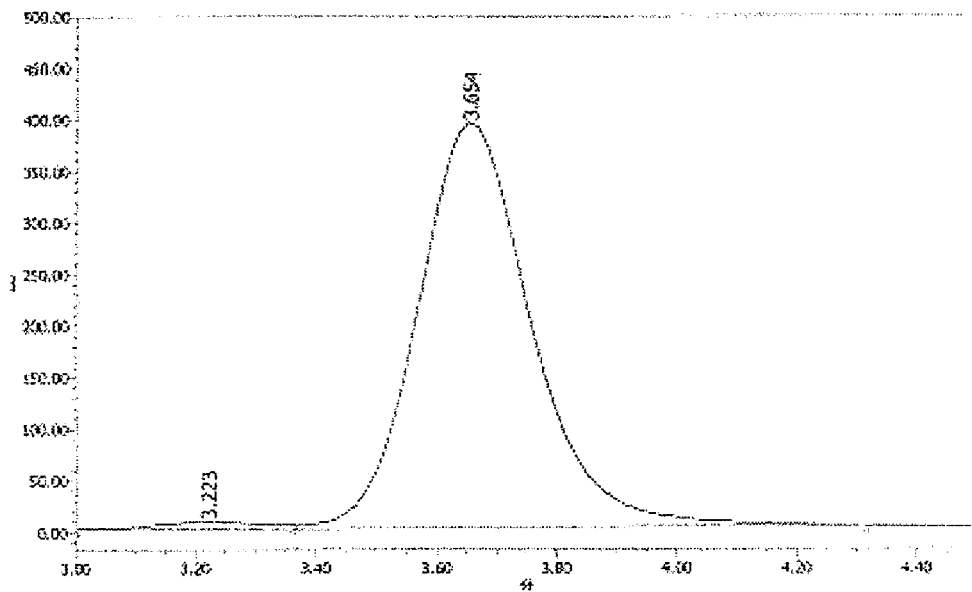

As a result, only in the cases of the samples treated with cABC, specific peaks were detected. The disaccharide composition profile of each sample was closely corresponding to the profile of the sample obtained by treating the chondroitin standard with cABC as shown in FIG. 6(A). Meanwhile, in the case where the chondroitin standard treated with cABC was mixed with Sample L treated with cABC, only one peak was detected, and thus Sample L was confirmed to be containing chondroitin (FIG. 6(B)). In the case of Sample E and S, the same results were obtained (data not shown).

Example 4

Preparation of KfoΔC/KfoA co-expression vector
<Amplification of kfoΔC Gene>
According to the method described in WO2007/145197, a DNA encoding the N-terminal-truncated KfoC comprising the nucleotide sequence of SEQ ID NO: 5 (kfoΔC gene) was cloned. The kfoΔC gene was inserted into pTrcHis to obtain pTrcHis-kfoΔC.

<Preparation of pTrcHis-kfoΔCA>

The plasmid pTrcHis-kfoCA prepared in the Example 1 was cleaved using restriction enzymes SphI and SmaI. DNA fragment (2.9 kDa) was obtained by digestion of the plasmid pTrcHis-kfoΔC using the same restriction enzymes. According to the conventional method, the DNA fragment was inserted into the SphI-SmaI site of the cleaved plasmid, and then the resulting plasmid was named pTrcHis-kfoΔCA.

Example 5

Preparation of Anti-KfoA and Anti-KfoC Antibodies
<Preparation of Anti-KfoA Antibodies>

Oligopeptide comprising the peptide sequence of SEQ ID No: 15 (CIVSR RDGDI AESWS SPEKA NK, Purity: >70%) was synthesized, and 4 mg of the oligopeptide was conjugated with KLH (keyhole limpet hemocyanin) by conventional method. After preparing the antigen solution by mixing with complete adjuvant, immunization was carried out 5 times in the interval for 2 weeks. The whole blood was collected, after antibody titre is confirmed. From each rabbit blood, anti-KfoA serum was obtained 48 mL (Sample A) and 60 mL (Sample B), respectively. After purification using Protein A column, IgG fraction EK-A was obtained 32 ml (IgG concentration: 5.30 mg/mL) from Sample A. <Preparation of Anti-KfoC Antibodies>

Oligopeptide comprising the peptide sequence of SEQ ID No: 16 (CQEPP GKENE TDRAA GK, Purity: >70%) was synthesized, and 4 mg of the oligopeptide was conjugated with KLH (keyhole limpet hemocyanin) by conventional method. After preparing the antigen solution by mixing with complete adjuvant, immunization was carried out 5 times in the interval for 2 weeks. The whole blood was collected, after antibody titre is confirmed. From each rabbit blood, anti-KfoA serum was obtained 65 mL (Sample A) and 39 mL (Sample B), respectively. After purification using Protein A column, IgG fraction EK-A was obtained 39 ml (IgG concentration: 4.41 mg/mL) from Sample A.

Example 6

In the same manner as in Example 2, the plasmid pTrcHis-kfo ΔCA was introduced into the E. coli K5 strain to obtain E. coli K5/pTrcHis-kfoΔCA strain, and the recombinant strain was cultured to evaluate the expression of the recombinant proteins.

The seed culture grown in LB medium supplemented with 100 ppm ampicillin (0.5 mL) was transferred into CYG medium supplemented with 100 ppm ampicillin (10 mL), and then the culture was carried out at 37° C. for 1.5 hours. After adding IPTG (final concentration: 1 mM), the cultivation was continued for further 4 hours. The bacterial cells were harvested from 900 μL of the culture and suspended into 90 μL of Laemmli buffer (×1). After heating in a boiling water bath for 10 min, 10 μL of the supernatant was subjected to SDS-PAGE in a 7.5% gel and transferred to a PVDF membrane, followed by Western analysis to detect expression of recombinant proteins. Anti-KfoA antibodies (EK-A) and anti-KfoC antibodies (EK-C) diluted to 1/1,000 was used as 1st antibody for detection of recombinant proteins KfoA, KfoC and KfoΔC. Anti-Rabbit Immunoglobulins HRP (DAKO,#PO448) was used as 2nd antibody. In addition, the same examinations using the culture of E. coli K5/pTrcHis-kfoCA and E. coli K5/pTrcHis-kfoA were carried out to compare the expression level of recombinant proteins. As a result, there was no the great difference on expression level of KfoA and KfoC (KfoΔC) between E. coli K5/pTrcHis-kfoCA and E. coli K5/pTrcHis-kfoA (FIG. 7).

Example 7

Preparation of Polysaccharide and its Detection by Disaccharide Analysis
<Preparation of Bacterial Cell>

In the same manner as in Example 3, bacterial cells and supernatant from the culture of E. coli K5/pTrcHis-kfoΔCA, E. coli K5/pTrcHis-kfoCA and E. coli K5/pTrcHis-kfoA strains were prepared after autoclaving at 121° C. for 5 min.
<Preparation of Polysaccharide Fraction>

The supernatant (1 mL) was dialyzed against running tap water overnight, and then dialyzed Solution was lyophilized. The lyophilized materials were dissolved into 100 μL of 50 mM Tris-HCl (pH8.0) to use as a polysaccharide fraction.
<Detection of Chondroitin by Disaccharide Analysis>

In the same manner as in Example 3, the obtained fraction was analyzed by the disaccharide composition analysis. Chondroitin standard solution (200 μg/mL and 100 μg/mL) was analyzed by the fluorescent HPLC to make the calibration curve of chondroitin. The relationship between chondroitin concentration and peak area of unsaturated double sugar, ΔDi-OS, was shown in Equation-1.

[Chondroitin;μg/mL of supernatant]=(0.000591× [Peak area]+1.219)/[concentration rate]
($r^2$=0.9984)   (Equation-1)

The peak agreed with unsaturated disaccharide (ΔDi-OS) was detected in the samples prepared from the E. coli K5/pTrcHis-kfo ΔCA and E. coli K5/pTrcHis-kfoCA (Data not shown). Table 1 shows the result of chondroitin concentration calculated using the Equation-1 in the recombinant cultures.

Table 1 Comparison of chondroitin content in the culture of the recombinant strains.

| E. coli K5 | Concentration | Peak area | Chondroitin [μg/mL] |
|---|---|---|---|
| K5/pTrcHis-kfoA | 10 | 10,187.4 | 0.7 |
| K5/pTrcHis-kfoCA | 10 | 505,032.3 | 30.0 |
| K5/pTrcHis-kfoΔCA | 10 | 888,677.6 | 52.6 |

By comparing chondroitin productivity between E. coli K5/pTrcHis-kfoΔCA and E. coli K5/pTrcHis-kfoCA, the recombinant strain E. coli K5/pTrcHis-kfoΔCA is more suitable for producing chondroitin by fermentation. This result suggested that chondroitin production could be enhanced by using the kfoΔC gene which encodes N-terminal-truncated KfoC.

INDUSTRIAL APPLICABILITY

By using the bacterium of the present invention, chondroitin and chondroitin sulfate can be produced at high efficiency and at low cost.

What is claimed is:

1. An isolated UDP-glucuronic acid-producing bacterium, which is introduced with a kfoA gene derived from the *Escherichia coli* K4 strain and a kfoC gene derived from *Escherichia coli* K4 strain, wherein said bacterium has chondroitin-producing ability, and wherein the kfoA gene encodes a protein selected from the group consisting of (A) and (B), and wherein the kfoC gene encodes a protein selected from the group consisting of (C), (D), (E) and (F):

(A) a protein comprising the amino acid sequence of SEQ ID NO: 2;

(B) a protein comprising the amino acid sequence of SEQ ID NO: 2 comprising substitution, deletion, insertion, or addition of 1-20 amino acids and having UDP-glucose-4-epimerase activity;

(C) a protein comprising the amino acid sequence of SEQ ID NO: 4;

(D) a protein comprising the amino acid sequence of SEQ ID NO: 4 comprising substitution, deletion, insertion, or addition of 1-20 amino acids and having chondroitin synthase activity;

(E) a protein comprising the amino acid sequence of SEQ ID NO: 6; and (F) a protein comprising the amino acid sequence of SEQ ID NO: 6 comprising substitution, deletion, insertion, or addition of 1-20 amino acids and having chondroitin synthase activity.

2. The bacterium according to claim 1, wherein the kfoA gene is a DNA selected from the group consisting of (a) and (b), and wherein the kfoC gene is a DNA selected from the group consisting of (c), (d), (e) and (f), and wherein stringent conditions are conditions for hybridization at 42° C. in a solution containing 50% formamide, 4×SSC, 50 mM HEPES (pH 7.0), 10×Denhardt's solution, 100 μg/ml salmon sperm DNA and washing with 2×SSC, 0.1% SDS solution at room temperature and then 0.1×SSC, 0.1% SDS solution at 60° C.:

(a) a DNA comprising the nucleotide sequence of SEQ ID NO: 1;

(b) a DNA that hybridizes with a DNA comprising the nucleotide sequence complementary to SEQ ID NO: 1 under stringent conditions and encodes a protein having UDP-glucose-4-epimerase activity;

(c) a DNA comprising the nucleotide sequence of SEQ ID NO: 3;

(d) a DNA that hybridizes with a DNA comprising the nucleotide sequence complementary to SEQ ID NO: 3 under stringent conditions and encodes a protein having chondroitin synthase activity;

(e) a DNA comprising the nucleotide sequence of SEQ ID NO: 5; and (f) a DNA that hybridizes with a DNA comprising the nucleotide sequence complementary to SEQ ID NO: 5 under stringent conditions and encodes a protein having chondroitin synthase activity.

3. The bacterium according to claim 1, wherein said bacterium is *Escherichia coli* K5 strain.

4. A method of producing chondroitin comprising at least the following steps (1) and (2):

(1) culturing the bacterium according to claims 1; and (2) collecting chondroitin from the culture.

5. A method of producing chondroitin sulfate comprising: producing chondroitin by the method according to claim 4; and sulfating the chondroitin to yield chondroitin sulfate.

6. A vector comprising a kfoA gene derived from *Escherichia coli* K4 strain and a kfoC gene derived from *Escherichia coli* K4 strain, wherein the kfoA gene is a DNA selected from the group consisting of (a) and (b), and wherein the kfoC gene is a DNA selected from the group consisting of (c), (d), (e) and (f), and wherein stringent conditions are conditions for hybridization at 42° C. in a solution containing 50% formamide, 4×SSC, 50 mM HEPES (pH 7.0), 10×Denhardt's solution, 100 μg/ml salmon sperm DNA and washing with 2×SSC, 0.1% SDS solution at room temperature and then 0.1×SSC, 0.1% SDS solution at 60° C.:
   (a) a DNA comprising the nucleotide sequence of SEQ ID NO: 1;
   (b) a DNA that hybridizes with a DNA comprising the nucleotide sequence complementary to SEQ ID NO: 1 under stringent conditions and encodes a protein having UDP-glucose-4-epimerase activity;
   (c) a DNA comprising the nucleotide sequence of SEQ ID NO: 3;
   (d) a DNA that hybridizes with a DNA comprising the nucleotide sequence complementary to SEQ ID NO: 3 under stringent conditions and encodes a protein having chondroitin synthase activity;
   (e) a DNA comprising the nucleotide sequence of SEQ ID NO: 5; and
   (f) a DNA that hybridizes with a DNA comprising the nucleotide sequence complementary to SEQ ID NO: 5 under stringent conditions and encodes a protein having chondroitin synthase activity.

* * * * *

UNITED STATES PATENT AND TRADEMARK OFFICE
CERTIFICATE OF CORRECTION

PATENT NO. : 8,283,145 B2
APPLICATION NO. : 12/596980
DATED : October 9, 2012
INVENTOR(S) : Suzuki et al.

It is certified that error appears in the above-identified patent and that said Letters Patent is hereby corrected as shown below:

On the Title Page
   In column 2 (page 1 item 56) at line 17, Under Other Publications, change "2005;16(4):378-84." to --2005; 16(4): 378-84.--.

In column 2 (page 1 item 56) at line 18, Under Other Publications, change "2007;143(3):212-23." to --2007; 143(3): 212-23.--.

In the Specifications:
   In column 3 at line 5, Change "51;" to --5;--.
   In column 3 at line 11 (approx.), Change "glucronic" to --glucuronic--.
   In column 3 at line 66, Change " kfo ⊿CA " to -- kfo⊿CA --.
   In column 4 at line 19, Change "meffloti," to --meliloti,--.
   In column 7 at line 5, Change "form" to --from--.
   In column 10 at line 43, Change "2275.)" to --2275)--.
   In column 11 at line 26-27, Delete "<Preparation of Anti-KfoC Antibodies>" and insert the same on Col. 11, Line 27, below "Sample A." as a heading.
   In column 11 at line 45, Change " kfo ⊿CA " to -- kfo⊿CA --.
   In column 11 at line 63, Change "(DAKO,#PO448)" to --(DAKO, #PO448)--.
   In column 11 at line 67, After "no" delete "the".
   In column 12 at line 19, Change "Solution" to --solution--.
   In column 12 at line 37, Change " kfo ⊿CA " to -- kfo⊿CA --.

Signed and Sealed this
Fourth Day of June, 2013

Teresa Stanek Rea
*Acting Director of the United States Patent and Trademark Office*

In the Claims:

In column 36 at line 66, In Claim 4, change "claims" to --claim--.

SEQUENCE LISTING

<160> NUMBER OF SEQ ID NOS: 16

<210> SEQ ID NO 1
<211> LENGTH: 1020
<212> TYPE: DNA
<213> ORGANISM: Escherichia coli
<220> FEATURE:
<221> NAME/KEY: CDS
<222> LOCATION: (1)..(1017)

<400> SEQUENCE: 1

```
atg aat ata tta gtt aca ggt gga gca ggc tat att ggc tcg cat act      48
Met Asn Ile Leu Val Thr Gly Gly Ala Gly Tyr Ile Gly Ser His Thr
1               5                   10                  15 agt tta tgt ctt ctg aat aaa ggt tac aat gtt gta atc att gac aac      96
Ser Leu Cys Leu Leu Asn Lys Gly Tyr Asn Val Val Ile Ile Asp Asn
            20                  25                  30 tta att aat tca tct tgc gag agc att cga agg att gaa tta ata gct     144
Leu Ile Asn Ser Ser Cys Glu Ser Ile Arg Arg Ile Glu Leu Ile Ala
        35                  40                  45 aaa aaa aaa gtt act ttc tat gag ttg aac atc aac aat gaa aaa gaa     192
Lys Lys Lys Val Thr Phe Tyr Glu Leu Asn Ile Asn Asn Glu Lys Glu
50                  55                  60 gtt aat caa att cta aaa aaa cac aaa ttt gat tgt ata atg cat ttt     240
Val Asn Gln Ile Leu Lys Lys His Lys Phe Asp Cys Ile Met His Phe
65                  70                  75                  80 gcc ggt gca aag tct gtt gct gaa tct tta ata aaa ccc att ttt tat     288
Ala Gly Ala Lys Ser Val Ala Glu Ser Leu Ile Lys Pro Ile Phe Tyr
                85                  90                  95 tat gat aat aat gtt tca ggg acg ttg caa tta att aat tgc gct ata     336
Tyr Asp Asn Asn Val Ser Gly Thr Leu Gln Leu Ile Asn Cys Ala Ile
            100                 105                 110 aaa aac gat gtg gct aat ttt att ttt agc tct tct gca acg gtt tat     384
Lys Asn Asp Val Ala Asn Phe Ile Phe Ser Ser Ser Ala Thr Val Tyr
        115                 120                 125 ggt gaa agc aaa ata atg cct gta aca gaa gat tgc cat ata gga gga     432
Gly Glu Ser Lys Ile Met Pro Val Thr Glu Asp Cys His Ile Gly Gly
130                 135                 140 aca tta aat cca tat ggt aca tca aag tat ata tca gaa ttg atg att     480
Thr Leu Asn Pro Tyr Gly Thr Ser Lys Tyr Ile Ser Glu Leu Met Ile
145                 150                 155                 160 aga gat att gca aaa aaa tat agc gat act aat ttt ttg tgt ctg aga     528
Arg Asp Ile Ala Lys Lys Tyr Ser Asp Thr Asn Phe Leu Cys Leu Arg
                165                 170                 175 tat ttt aac cca aca ggt gct cac gag tcg gga atg atc ggt gaa agt     576
Tyr Phe Asn Pro Thr Gly Ala His Glu Ser Gly Met Ile Gly Glu Ser
            180                 185                 190 ccc gct gat ata cca agc aat tta gtt cct tat ata tta caa gtt gct     624
Pro Ala Asp Ile Pro Ser Asn Leu Val Pro Tyr Ile Leu Gln Val Ala
        195                 200                 205 atg ggt aaa cta gaa aaa ctt atg gtg ttt ggg gga gat tac cct aca     672
Met Gly Lys Leu Glu Lys Leu Met Val Phe Gly Gly Asp Tyr Pro Thr
210                 215                 220 aag gat gga acc ggt gtt cgt gat tat ata cac gta atg gat tta gcg     720
Lys Asp Gly Thr Gly Val Arg Asp Tyr Ile His Val Met Asp Leu Ala
225                 230                 235                 240 gaa ggg cat gtg gct gct tta tct tac ctt ttc cgt gat aat aac act     768
Glu Gly His Val Ala Ala Leu Ser Tyr Leu Phe Arg Asp Asn Asn Thr
                245                 250                 255 aat tat cat gtt ttt aat tta ggt act ggt aaa gga tat tct gtt tta     816
Asn Tyr His Val Phe Asn Leu Gly Thr Gly Lys Gly Tyr Ser Val Leu
```

```
gag ctg gtt tct acc ttt gaa aaa ata tct ggg gtt aga att cca tat      864
Glu Leu Val Ser Thr Phe Glu Lys Ile Ser Gly Val Arg Ile Pro Tyr
        275                 280                 285 gaa att gtt tcg aga aga gat ggg gat att gct gaa agt tgg tca tca      912
Glu Ile Val Ser Arg Arg Asp Gly Asp Ile Ala Glu Ser Trp Ser Ser
    290                 295                 300 cca gaa aaa gca aat aag tat ctc aat tgg aaa gct aaa agg gaa ttg      960
Pro Glu Lys Ala Asn Lys Tyr Leu Asn Trp Lys Ala Lys Arg Glu Leu
305                 310                 315                 320 gaa aca atg ctt gag gat gcc tgg cgc tgg caa atg aaa aac cca aat     1008
Glu Thr Met Leu Glu Asp Ala Trp Arg Trp Gln Met Lys Asn Pro Asn
                325                 330                 335 ggt tat att taa                                                     1020
Gly Tyr Ile
```

<210> SEQ ID NO 2
<211> LENGTH: 339
<212> TYPE: PRT
<213> ORGANISM: Escherichia coli

<400> SEQUENCE: 2

```
Met Asn Ile Leu Val Thr Gly Gly Ala Gly Tyr Ile Gly Ser His Thr
1               5                   10                  15

Ser Leu Cys Leu Leu Asn Lys Gly Tyr Asn Val Ile Ile Asp Asn
            20                  25                  30      Asn

Leu Ile Asn Ser Ser Cys Glu Ser Ile Arg Arg Ile Glu Leu Ile Ala
        35                  40                  45

Lys Lys Lys Val Thr Phe Tyr Glu Leu Asn Ile Asn Asn Glu Lys Glu
50                  55                  60

Val Asn Gln Ile Leu Lys Lys His Lys Phe Asp Cys Ile Met His Phe
65                  70                  75                  80

Ala Gly Ala Lys Ser Val Ala Glu Ser Leu Ile Lys Pro Ile Phe Tyr
                85                  90                  95

Tyr Asp Asn Asn Val Ser Gly Thr Leu Gln Leu Ile Asn Cys Ala Ile
            100                 105                 110

Lys Asn Asp Val Ala Asn Phe Ile Phe Ser Ser Ala Thr Val Tyr
        115                 120                 125

Gly Glu Ser Lys Ile Met Pro Val Thr Glu Asp Cys His Ile Gly Gly
    130                 135                 140

Thr Leu Asn Pro Tyr Gly Thr Ser Lys Tyr Ile Ser Glu Leu Met Ile
145                 150                 155                 160

Arg Asp Ile Ala Lys Lys Tyr Ser Asp Thr Asn Phe Leu Cys Leu Arg
                165                 170                 175

Tyr Phe Asn Pro Thr Gly Ala His Glu Ser Gly Met Ile Gly Glu Ser
            180                 185                 190

Pro Ala Asp Ile Pro Ser Asn Leu Val Pro Tyr Ile Leu Gln Val Ala
        195                 200                 205

Met Gly Lys Leu Glu Lys Leu Met Val Phe Gly Gly Asp Tyr Pro Thr
    210                 215                 220

Lys Asp Gly Thr Gly Val Arg Asp Tyr Ile His Val Met Asp Leu Ala
225                 230                 235                 240

Glu Gly His Val Ala Ala Leu Ser Tyr Leu Phe Arg Asp Asn Thr
                245                 250                 255

Asn Tyr His Val Phe Asn Leu Gly Thr Gly Lys Gly Tyr Ser Val Leu
            260                 265                 270
```

-continued

```
Glu Leu Val Ser Thr Phe Glu Lys Ile Ser Gly Val Arg Ile Pro Tyr
            275                 280                 285

Glu Ile Val Ser Arg Arg Asp Gly Asp Ile Ala Glu Ser Trp Ser Ser
            290                 295                 300

Pro Glu Lys Ala Asn Lys Tyr Leu Asn Trp Lys Ala Lys Arg Glu Leu
305                 310                 315                 320

Glu Thr Met Leu Glu Asp Ala Trp Arg Trp Gln Met Lys Asn Pro Asn
            325                 330                 335

Gly Tyr Ile

<210> SEQ ID NO 3
<211> LENGTH: 2061
<212> TYPE: DNA
<213> ORGANISM: Escherichia coli
<220> FEATURE:
<221> NAME/KEY: CDS
<222> LOCATION: (1)..(2058)

<400> SEQUENCE: 3
```

| | | |
|---|---|---|
| atg agt att ctt aat caa gca ata aat tta tat aaa aac aaa aat tat<br>Met Ser Ile Leu Asn Gln Ala Ile Asn Leu Tyr Lys Asn Lys Asn Tyr<br>1                   5                   10                15 | | 48 |
| cgc caa gct tta tct ctt ttt gag aag gtt gct gaa att tat gat gtt<br>Arg Gln Ala Leu Ser Leu Phe Glu Lys Val Ala Glu Ile Tyr Asp Val<br>           20                   25                  30 | | 96 |
| agt tgg gtc gaa gca aat ata aaa tta tgc caa acc gca ctc aat ctt<br>Ser Trp Val Glu Ala Asn Ile Lys Leu Cys Gln Thr Ala Leu Asn Leu<br>               35                   40                45 | | 144 |
| tct gaa gaa gtt gat aag tta aat cgt aaa gct gtt att gat att gat<br>Ser Glu Glu Val Asp Lys Leu Asn Arg Lys Ala Val Ile Asp Ile Asp<br>    50                   55                   60 | | 192 |
| gca gca aca aaa ata atg tgt tct aac gcc aaa gca att agt ctg aac<br>Ala Ala Thr Lys Ile Met Cys Ser Asn Ala Lys Ala Ile Ser Leu Asn<br>65                   70                   75                80 | | 240 |
| gag gtt gaa aaa aat gaa ata ata agc aaa tac cga gaa ata acc gca<br>Glu Val Glu Lys Asn Glu Ile Ile Ser Lys Tyr Arg Glu Ile Thr Ala<br>                   85                   90                95 | | 288 |
| aag aaa tca gaa cgg gcg gag tta aag gaa gtc gaa ccc att cct tta<br>Lys Lys Ser Glu Arg Ala Glu Leu Lys Glu Val Glu Pro Ile Pro Leu<br>           100                  105               110 | | 336 |
| gat tgg cct agt gat tta act tta ccg ccg tta cct gag agc aca aac<br>Asp Trp Pro Ser Asp Leu Thr Leu Pro Pro Leu Pro Glu Ser Thr Asn<br>            115                120               125 | | 384 |
| gat tat gtt tgg gcg ggg aaa aga aaa gag ctt gat gat tat cca aga<br>Asp Tyr Val Trp Ala Gly Lys Arg Lys Glu Leu Asp Asp Tyr Pro Arg<br>     130                 135                140 | | 432 |
| aaa cag tta atc att gac ggg ctt agt att gta att cct aca tat aat<br>Lys Gln Leu Ile Ile Asp Gly Leu Ser Ile Val Ile Pro Thr Tyr Asn<br>145                   150                155                160 | | 480 |
| cga gca aaa ata ctt gca att aca ctt gct tgt ctt tgt aac caa aag<br>Arg Ala Lys Ile Leu Ala Ile Thr Leu Ala Cys Leu Cys Asn Gln Lys<br>                  165                170               175 | | 528 |
| acc ata tac gac tat gaa gtt att gtt gcc gat gat gga agt aaa gaa<br>Thr Ile Tyr Asp Tyr Glu Val Ile Val Ala Asp Asp Gly Ser Lys Glu<br>                180                185               190 | | 576 |
| aat att gaa gaa ata gta aga gaa ttt gaa agt tta tta aat ata aaa<br>Asn Ile Glu Glu Ile Val Arg Glu Phe Glu Ser Leu Leu Asn Ile Lys<br>           195                  200               205 | | 624 |
| tat gta cgt cag aag gat tat gga tat caa ctg tgt gct gtt aga aat<br>Tyr Val Arg Gln Lys Asp Tyr Gly Tyr Gln Leu Cys Ala Val Arg Asn | | 672 |

-continued

```
       210                 215                 220
ctt ggg ctt agg gct gca aag tat aat tat gtt gca att ctg gat tgt    720
Leu Gly Leu Arg Ala Ala Lys Tyr Asn Tyr Val Ala Ile Leu Asp Cys
225                 230                 235                 240 gat atg gct ccg aac cca cta tgg gtt cag tca tat atg gaa cta tta    768
Asp Met Ala Pro Asn Pro Leu Trp Val Gln Ser Tyr Met Glu Leu Leu
                245                 250                 255 gcg gtg gac gat aat gtt gct cta att ggc cct aga aaa tat ata gat    816
Ala Val Asp Asp Asn Val Ala Leu Ile Gly Pro Arg Lys Tyr Ile Asp
            260                 265                 270 aca agc aag cat aca tat tta gat ttc ctt tcc caa aaa tca cta ata    864
Thr Ser Lys His Thr Tyr Leu Asp Phe Leu Ser Gln Lys Ser Leu Ile
        275                 280                 285 aat gaa att cct gaa atc att act aat aat cag gtt gca ggc aag gtt    912
Asn Glu Ile Pro Glu Ile Ile Thr Asn Asn Gln Val Ala Gly Lys Val
    290                 295                 300 gag caa aac aaa tca gtt gac tgg cga ata gaa cat ttc aaa aat acc    960
Glu Gln Asn Lys Ser Val Asp Trp Arg Ile Glu His Phe Lys Asn Thr
305                 310                 315                 320 gat aat cta aga tta tgc aac aca cca ttt cga ttt ttt agc gga ggt   1008
Asp Asn Leu Arg Leu Cys Asn Thr Pro Phe Arg Phe Phe Ser Gly Gly
                325                 330                 335 aat gtc gct ttt gcg aaa aaa tgg ctt ttc cgt gca gga tgg ttt gat   1056
Asn Val Ala Phe Ala Lys Lys Trp Leu Phe Arg Ala Gly Trp Phe Asp
            340                 345                 350 gaa gag ttt acg cat tgg ggg ggg gag gat aat gag ttt gga tat cgt   1104
Glu Glu Phe Thr His Trp Gly Gly Glu Asp Asn Glu Phe Gly Tyr Arg
        355                 360                 365 ctc tac aga gaa gga tgt tac ttt cgg tct gtt gaa gga gca atg gca   1152
Leu Tyr Arg Glu Gly Cys Tyr Phe Arg Ser Val Glu Gly Ala Met Ala
    370                 375                 380 tat cat caa gaa cca ccc ggg aaa gaa aac gag acg gat cgt gcg gca   1200
Tyr His Gln Glu Pro Pro Gly Lys Glu Asn Glu Thr Asp Arg Ala Ala
385                 390                 395                 400 ggg aaa aat att act gtt caa ttg tta cag caa aaa gtt cct tat ttc   1248
Gly Lys Asn Ile Thr Val Gln Leu Leu Gln Gln Lys Val Pro Tyr Phe
                405                 410                 415 tat aga aaa aaa gaa aaa ata gaa tcc gcg aca tta aaa aga gta cca   1296
Tyr Arg Lys Lys Glu Lys Ile Glu Ser Ala Thr Leu Lys Arg Val Pro
            420                 425                 430 cta gta tct ata tat att ccc gcc tat aac tgc tct aaa tat att gtt   1344
Leu Val Ser Ile Tyr Ile Pro Ala Tyr Asn Cys Ser Lys Tyr Ile Val
        435                 440                 445 cgt tgt gtt gaa agc gcc ctt aat cag aca ata act gac tta gaa gta   1392
Arg Cys Val Glu Ser Ala Leu Asn Gln Thr Ile Thr Asp Leu Glu Val
    450                 455                 460 tgc ata tgc gat gat ggt tcc aca gat gat aca ttg cgg att ctt cag   1440
Cys Ile Cys Asp Asp Gly Ser Thr Asp Asp Thr Leu Arg Ile Leu Gln
465                 470                 475                 480 gag cat tat gca aac cat cct cga gtt cgt ttt att tca caa aaa aac   1488
Glu His Tyr Ala Asn His Pro Arg Val Arg Phe Ile Ser Gln Lys Asn
                485                 490                 495 aaa gga att ggt tca gca tct aat aca gca gtt aga ttg tgt cgg gga   1536
Lys Gly Ile Gly Ser Ala Ser Asn Thr Ala Val Arg Leu Cys Arg Gly
            500                 505                 510 ttc tat ata ggt cag tta gac tct gat gac ttt ctt gaa cca gat gct   1584
Phe Tyr Ile Gly Gln Leu Asp Ser Asp Asp Phe Leu Glu Pro Asp Ala
        515                 520                 525 gtt gaa cta tgt cta gat gaa ttt aga aaa gat cta tca ttg gca tgt   1632
Val Glu Leu Cys Leu Asp Glu Phe Arg Lys Asp Leu Ser Leu Ala Cys
```

```
                    530              535              540
gtt tat aca act aac cgt aat ata gat cgt gaa ggt aat ttg ata tca    1680
Val Tyr Thr Thr Asn Arg Asn Ile Asp Arg Glu Gly Asn Leu Ile Ser
545                 550              555              560 aat ggc tat aat tgg ccc att tat tcg cga gaa aaa ctt act agt gca    1728
Asn Gly Tyr Asn Trp Pro Ile Tyr Ser Arg Glu Lys Leu Thr Ser Ala
                565              570              575 atg ata tgt cat cat ttc agg atg ttc aca gca aga gca tgg aac cta    1776
Met Ile Cys His His Phe Arg Met Phe Thr Ala Arg Ala Trp Asn Leu
            580              585              590 act gaa ggt ttc aac gaa tcg atc agc aac gca gtt gat tac gat atg    1824
Thr Glu Gly Phe Asn Glu Ser Ile Ser Asn Ala Val Asp Tyr Asp Met
        595              600              605 tat tta aaa ctt agt gaa gtt gga ccg ttc aag cat ata aac aaa att    1872
Tyr Leu Lys Leu Ser Glu Val Gly Pro Phe Lys His Ile Asn Lys Ile
    610              615              620 tgt tat aat cgc gta ttg cat ggt gaa aat acg tct ata aaa aag ttg    1920
Cys Tyr Asn Arg Val Leu His Gly Glu Asn Thr Ser Ile Lys Lys Leu
625              630              635              640 gat att caa aag gaa aat cat ttt aaa gtt gtt aac gaa tca tta agt    1968
Asp Ile Gln Lys Glu Asn His Phe Lys Val Val Asn Glu Ser Leu Ser
                645              650              655 agg cta ggc ata aaa aaa tat aaa tat tca cca tta act aat ttg aat    2016
Arg Leu Gly Ile Lys Lys Tyr Lys Tyr Ser Pro Leu Thr Asn Leu Asn
            660              665              670 gaa tgt aga aaa tat acc tgg gaa aaa ata gag aat gat tta taa        2061
Glu Cys Arg Lys Tyr Thr Trp Glu Lys Ile Glu Asn Asp Leu
        675              680              685

<210> SEQ ID NO 4
<211> LENGTH: 686
<212> TYPE: PRT
<213> ORGANISM: Escherichia coli

<400> SEQUENCE: 4

Met Ser Ile Leu Asn Gln Ala Ile Asn Leu Tyr Lys Asn Lys Asn Tyr
1               5                   10                  15

Arg Gln Ala Leu Ser Leu Phe Glu Lys Val Ala Glu Ile Tyr Asp Val
            20                  25                  30

Ser Trp Val Glu Ala Asn Ile Lys Leu Cys Gln Thr Ala Leu Asn Leu
        35                  40                  45

Ser Glu Glu Val Asp Lys Leu Asn Arg Lys Ala Val Ile Asp Ile Asp
    50                  55                  60

Ala Ala Thr Lys Ile Met Cys Ser Asn Ala Lys Ala Ile Ser Leu Asn
65                  70                  75                  80

Glu Val Glu Lys Asn Glu Ile Ile Ser Lys Tyr Arg Glu Ile Thr Ala
                85                  90                  95

Lys Lys Ser Glu Arg Ala Glu Leu Lys Glu Val Glu Pro Ile Pro Leu
            100                 105                 110

Asp Trp Pro Ser Asp Leu Thr Leu Pro Pro Leu Pro Glu Ser Thr Asn
        115                 120                 125

Asp Tyr Val Trp Ala Gly Lys Arg Lys Glu Leu Asp Asp Tyr Pro Arg
    130                 135                 140

Lys Gln Leu Ile Ile Asp Gly Leu Ser Ile Val Ile Pro Thr Tyr Asn
145                 150                 155                 160

Arg Ala Lys Ile Leu Ala Ile Thr Leu Ala Cys Leu Cys Asn Gln Lys
                165                 170                 175

Thr Ile Tyr Asp Tyr Glu Val Ile Val Ala Asp Asp Gly Ser Lys Glu
```

```
                180                 185                 190
Asn Ile Glu Glu Ile Val Arg Glu Phe Glu Ser Leu Leu Asn Ile Lys
                195                 200                 205
Tyr Val Arg Gln Lys Asp Tyr Gly Tyr Gln Leu Cys Ala Val Arg Asn
            210                 215                 220
Leu Gly Leu Arg Ala Ala Lys Tyr Asn Tyr Val Ala Ile Leu Asp Cys
225                 230                 235                 240
Asp Met Ala Pro Asn Pro Leu Trp Val Gln Ser Tyr Met Glu Leu Leu
                245                 250                 255
Ala Val Asp Asp Asn Val Ala Leu Ile Gly Pro Arg Lys Tyr Ile Asp
                260                 265                 270
Thr Ser Lys His Thr Tyr Leu Asp Phe Leu Ser Gln Lys Ser Leu Ile
            275                 280                 285
Asn Glu Ile Pro Glu Ile Ile Thr Asn Asn Gln Val Ala Gly Lys Val
            290                 295                 300
Glu Gln Asn Lys Ser Val Asp Trp Arg Ile Glu His Phe Lys Asn Thr
305                 310                 315                 320
Asp Asn Leu Arg Leu Cys Asn Thr Pro Phe Arg Phe Ser Gly Gly
                325                 330                 335
Asn Val Ala Phe Ala Lys Lys Trp Leu Phe Arg Ala Gly Trp Phe Asp
                340                 345                 350
Glu Glu Phe Thr His Trp Gly Gly Glu Asp Asn Glu Phe Gly Tyr Arg
            355                 360                 365
Leu Tyr Arg Glu Gly Cys Tyr Phe Arg Ser Val Glu Gly Ala Met Ala
    370                 375                 380
Tyr His Gln Glu Pro Pro Gly Lys Glu Asn Glu Thr Asp Arg Ala Ala
385                 390                 395                 400
Gly Lys Asn Ile Thr Val Gln Leu Leu Gln Gln Lys Val Pro Tyr Phe
                405                 410                 415
Tyr Arg Lys Lys Glu Lys Ile Glu Ser Ala Thr Leu Lys Arg Val Pro
            420                 425                 430
Leu Val Ser Ile Tyr Ile Pro Ala Tyr Asn Cys Ser Lys Tyr Ile Val
            435                 440                 445
Arg Cys Val Glu Ser Ala Leu Asn Gln Thr Ile Thr Asp Leu Glu Val
        450                 455                 460
Cys Ile Cys Asp Asp Gly Ser Thr Asp Thr Leu Arg Ile Leu Gln
465                 470                 475                 480
Glu His Tyr Ala Asn His Pro Arg Val Arg Phe Ile Ser Gln Lys Asn
                485                 490                 495
Lys Gly Ile Gly Ser Ala Ser Asn Thr Ala Val Arg Leu Cys Arg Gly
            500                 505                 510
Phe Tyr Ile Gly Gln Leu Asp Ser Asp Asp Phe Leu Glu Pro Asp Ala
        515                 520                 525
Val Glu Leu Cys Leu Asp Glu Phe Arg Lys Asp Leu Ser Leu Ala Cys
            530                 535                 540
Val Tyr Thr Thr Asn Arg Asn Ile Asp Arg Glu Gly Asn Leu Ile Ser
545                 550                 555                 560
Asn Gly Tyr Asn Trp Pro Ile Tyr Ser Arg Glu Lys Leu Thr Ser Ala
                565                 570                 575
Met Ile Cys His His Phe Arg Met Phe Thr Ala Arg Ala Trp Asn Leu
            580                 585                 590
Thr Glu Gly Phe Asn Glu Ser Ile Ser Asn Ala Val Asp Tyr Asp Met
        595                 600                 605
```

-continued

| | | | | | | | | | | | | |
|---|---|---|---|---|---|---|---|---|---|---|---|---|
|Tyr|Leu|Lys|Leu|Ser|Glu|Val|Gly|Pro|Phe|Lys|His|Ile|Asn|Lys|Ile|
| |610| | | |615| | | |620| | | | | | |

| | | | | | | | | | | | | | | | |
|---|---|---|---|---|---|---|---|---|---|---|---|---|---|---|---|
|Cys|Tyr|Asn|Arg|Val|Leu|His|Gly|Glu|Asn|Thr|Ser|Ile|Lys|Lys|Leu|
|625| | | | |630| | | | |635| | | | |640|

| | | | | | | | | | | | | | | | |
|---|---|---|---|---|---|---|---|---|---|---|---|---|---|---|---|
|Asp|Ile|Gln|Lys|Glu|Asn|His|Phe|Lys|Val|Val|Asn|Glu|Ser|Leu|Ser|
| | | | |645| | | | |650| | | | |655| |

| | | | | | | | | | | | | | | | |
|---|---|---|---|---|---|---|---|---|---|---|---|---|---|---|---|
|Arg|Leu|Gly|Ile|Lys|Lys|Tyr|Lys|Tyr|Ser|Pro|Leu|Thr|Asn|Leu|Asn|
| | | | |660| | | | |665| | | | |670| |

| | | | | | | | | | | |
|---|---|---|---|---|---|---|---|---|---|---|
|Glu|Cys|Arg|Lys|Tyr|Thr|Trp|Glu|Lys|Ile|Glu|Asn|Asp|Leu|
| | | |675| | | | |680| | | | |685|

```
<210> SEQ ID NO 5
<211> LENGTH: 1890
<212> TYPE: DNA
<213> ORGANISM: Escherichia coli
<220> FEATURE:
<221> NAME/KEY: CDS
<222> LOCATION: (1)..(1887)

<400> SEQUENCE: 5
```

| | | | | | | | | | | | | | | | | |
|---|---|---|---|---|---|---|---|---|---|---|---|---|---|---|---|---|
|aaa|gct|gtt|att|gat|att|gat|gca|gca|aca|aaa|ata|atg|tgt|tct|aac|48|
|Lys|Ala|Val|Ile|Asp|Ile|Asp|Ala|Ala|Thr|Lys|Ile|Met|Cys|Ser|Asn| |
|1| | | |5| | | | |10| | | | |15| | |

| | | | | | | | | | | | | | | | | |
|---|---|---|---|---|---|---|---|---|---|---|---|---|---|---|---|---|
|gcc|aaa|gca|att|agt|ctg|aac|gag|gtt|gaa|aaa|aat|gaa|ata|ata|agc|96|
|Ala|Lys|Ala|Ile|Ser|Leu|Asn|Glu|Val|Glu|Lys|Asn|Glu|Ile|Ile|Ser| |
| | | |20| | | | |25| | | | |30| | | |

| | | | | | | | | | | | | | | | | |
|---|---|---|---|---|---|---|---|---|---|---|---|---|---|---|---|---|
|aaa|tac|cga|gaa|ata|acc|gca|aag|aaa|tca|gaa|cgg|gcg|gag|tta|aag|144|
|Lys|Tyr|Arg|Glu|Ile|Thr|Ala|Lys|Lys|Ser|Glu|Arg|Ala|Glu|Leu|Lys| |
| | |35| | | | |40| | | | |45| | | | |

| | | | | | | | | | | | | | | | | |
|---|---|---|---|---|---|---|---|---|---|---|---|---|---|---|---|---|
|gaa|gtc|gaa|ccc|att|cct|tta|gat|tgg|cct|agt|gat|tta|act|tta|ccg|192|
|Glu|Val|Glu|Pro|Ile|Pro|Leu|Asp|Trp|Pro|Ser|Asp|Leu|Thr|Leu|Pro| |
|50| | | | |55| | | | |60| | | | | | |

| | | | | | | | | | | | | | | | | |
|---|---|---|---|---|---|---|---|---|---|---|---|---|---|---|---|---|
|ccg|tta|cct|gag|agc|aca|aac|gat|tat|gtt|tgg|gcg|ggg|aaa|aga|aaa|240|
|Pro|Leu|Pro|Glu|Ser|Thr|Asn|Asp|Tyr|Val|Trp|Ala|Gly|Lys|Arg|Lys| |
|65| | | | |70| | | | |75| | | | |80| |

| | | | | | | | | | | | | | | | | |
|---|---|---|---|---|---|---|---|---|---|---|---|---|---|---|---|---|
|gag|ctt|gat|gat|tat|cca|aga|aaa|cag|tta|atc|att|gac|ggg|ctt|agt|288|
|Glu|Leu|Asp|Asp|Tyr|Pro|Arg|Lys|Gln|Leu|Ile|Ile|Asp|Gly|Leu|Ser| |
| | | | |85| | | | |90| | | | |95| | |

| | | | | | | | | | | | | | | | | |
|---|---|---|---|---|---|---|---|---|---|---|---|---|---|---|---|---|
|att|gta|att|cct|aca|tat|aat|cga|gca|aaa|ata|ctt|gca|att|aca|ctt|336|
|Ile|Val|Ile|Pro|Thr|Tyr|Asn|Arg|Ala|Lys|Ile|Leu|Ala|Ile|Thr|Leu| |
| | | |100| | | | |105| | | | |110| | | |

| | | | | | | | | | | | | | | | | |
|---|---|---|---|---|---|---|---|---|---|---|---|---|---|---|---|---|
|gct|tgt|ctt|tgt|aac|caa|aag|acc|ata|tac|gac|tat|gaa|gtt|att|gtt|384|
|Ala|Cys|Leu|Cys|Asn|Gln|Lys|Thr|Ile|Tyr|Asp|Tyr|Glu|Val|Ile|Val| |
| | |115| | | | |120| | | | |125| | | | |

| | | | | | | | | | | | | | | | | |
|---|---|---|---|---|---|---|---|---|---|---|---|---|---|---|---|---|
|gcc|gat|gat|gga|agt|aaa|gaa|aat|att|gaa|gaa|ata|gta|aga|gaa|ttt|432|
|Ala|Asp|Asp|Gly|Ser|Lys|Glu|Asn|Ile|Glu|Glu|Ile|Val|Arg|Glu|Phe| |
|130| | | | |135| | | | |140| | | | | | |

| | | | | | | | | | | | | | | | | |
|---|---|---|---|---|---|---|---|---|---|---|---|---|---|---|---|---|
|gaa|agt|tta|tta|aat|ata|aaa|tat|gta|cgt|cag|aag|gat|tat|gga|tat|480|
|Glu|Ser|Leu|Leu|Asn|Ile|Lys|Tyr|Val|Arg|Gln|Lys|Asp|Tyr|Gly|Tyr| |
|145| | | | |150| | | | |155| | | | |160| |

| | | | | | | | | | | | | | | | | |
|---|---|---|---|---|---|---|---|---|---|---|---|---|---|---|---|---|
|caa|ctg|tgt|gct|gtt|aga|aat|ctt|ggg|ctt|agg|gct|gca|aag|tat|aat|528|
|Gln|Leu|Cys|Ala|Val|Arg|Asn|Leu|Gly|Leu|Arg|Ala|Ala|Lys|Tyr|Asn| |
| | | |165| | | | |170| | | | |175| | | |

| | | | | | | | | | | | | | | | | |
|---|---|---|---|---|---|---|---|---|---|---|---|---|---|---|---|---|
|tat|gtt|gca|att|ctg|gat|tgt|gat|atg|gct|ccg|aac|cca|cta|tgg|gtt|576|
|Tyr|Val|Ala|Ile|Leu|Asp|Cys|Asp|Met|Ala|Pro|Asn|Pro|Leu|Trp|Val| |
| | | | |180| | | | |185| | | | |190| | |

| | | | | | | | | | | | | | | | | |
|---|---|---|---|---|---|---|---|---|---|---|---|---|---|---|---|---|
|cag|tca|tat|atg|gaa|cta|tta|gcg|gtg|gac|gat|aat|gtt|gct|cta|att|624|
|Gln|Ser|Tyr|Met|Glu|Leu|Leu|Ala|Val|Asp|Asp|Asn|Val|Ala|Leu|Ile| |
| | | |195| | | | |200| | | | |205| | | |

| | | | | | | | | | | | | | | | | |
|---|---|---|---|---|---|---|---|---|---|---|---|---|---|---|---|---|
|ggc|cct|aga|aaa|tat|ata|gat|aca|agc|aag|cat|aca|tat|tta|gat|ttc|672|
|Gly|Pro|Arg|Lys|Tyr|Ile|Asp|Thr|Ser|Lys|His|Thr|Tyr|Leu|Asp|Phe| |

-continued

```
                 210                 215                 220
ctt tcc caa aaa tca cta ata aat gaa att cct gaa atc att act aat       720
Leu Ser Gln Lys Ser Leu Ile Asn Glu Ile Pro Glu Ile Ile Thr Asn
225                 230                 235                 240 aat cag gtt gca ggc aag gtt gag caa aac aaa tca gtt gac tgg cga       768
Asn Gln Val Ala Gly Lys Val Glu Gln Asn Lys Ser Val Asp Trp Arg
                245                 250                 255 ata gaa cat ttc aaa aat acc gat aat cta aga tta tgc aac aca cca       816
Ile Glu His Phe Lys Asn Thr Asp Asn Leu Arg Leu Cys Asn Thr Pro
                260                 265                 270 ttt cga ttt ttt agc gga ggt aat gtc gct ttt gcg aaa aaa tgg ctt       864
Phe Arg Phe Phe Ser Gly Gly Asn Val Ala Phe Ala Lys Lys Trp Leu
                275                 280                 285 ttc cgt gca gga tgg ttt gat gaa gag ttt acg cat tgg ggg ggg gag       912
Phe Arg Ala Gly Trp Phe Asp Glu Glu Phe Thr His Trp Gly Gly Glu
290                 295                 300 gat aat gag ttt gga tat cgt ctc tac aga gaa gga tgt tac ttt cgg       960
Asp Asn Glu Phe Gly Tyr Arg Leu Tyr Arg Glu Gly Cys Tyr Phe Arg
305                 310                 315                 320 tct gtt gaa gga gca atg gca tat cat caa gaa cca ccc ggg aaa gaa      1008
Ser Val Glu Gly Ala Met Ala Tyr His Gln Glu Pro Pro Gly Lys Glu
                325                 330                 335 aac gag acg gat cgt gcg gca ggg aaa aat att act gtt caa ttg tta      1056
Asn Glu Thr Asp Arg Ala Ala Gly Lys Asn Ile Thr Val Gln Leu Leu
                340                 345                 350 cag caa aaa gtt cct tat ttc tat aga aaa aaa gaa aaa ata gaa tcc      1104
Gln Gln Lys Val Pro Tyr Phe Tyr Arg Lys Lys Glu Lys Ile Glu Ser
                355                 360                 365 gcg aca tta aaa aga gta cca cta gta tct ata tat att ccc gcc tat      1152
Ala Thr Leu Lys Arg Val Pro Leu Val Ser Ile Tyr Ile Pro Ala Tyr
370                 375                 380 aac tgc tct aaa tat att gtt cgt tgt gtt gaa agc gcc ctt aat cag      1200
Asn Cys Ser Lys Tyr Ile Val Arg Cys Val Glu Ser Ala Leu Asn Gln
385                 390                 395                 400 aca ata act gac tta gaa gta tgc ata tgc gat gat ggt tcc aca gat      1248
Thr Ile Thr Asp Leu Glu Val Cys Ile Cys Asp Asp Gly Ser Thr Asp
                405                 410                 415 gat aca ttg cgg att ctt cag gag cat tat gca aac cat cct cga gtt      1296
Asp Thr Leu Arg Ile Leu Gln Glu His Tyr Ala Asn His Pro Arg Val
                420                 425                 430 cgt ttt att tca caa aaa aac aaa gga att ggt tca gca tct aat aca      1344
Arg Phe Ile Ser Gln Lys Asn Lys Gly Ile Gly Ser Ala Ser Asn Thr
                435                 440                 445 gca gtt aga ttg tgt cgg gga ttc tat ata ggt cag tta gac tct gat      1392
Ala Val Arg Leu Cys Arg Gly Phe Tyr Ile Gly Gln Leu Asp Ser Asp
450                 455                 460 gac ttt ctt gaa cca gat gct gtt gaa cta tgt cta gat gaa ttt aga      1440
Asp Phe Leu Glu Pro Asp Ala Val Glu Leu Cys Leu Asp Glu Phe Arg
465                 470                 475                 480 aaa gat cta tca ttg gca tgt gtt tat aca act aac cgt aat ata gat      1488
Lys Asp Leu Ser Leu Ala Cys Val Tyr Thr Thr Asn Arg Asn Ile Asp
                485                 490                 495 cgt gaa ggt aat ttg ata tca aat ggc tat aat tgg ccc att tat tcg      1536
Arg Glu Gly Asn Leu Ile Ser Asn Gly Tyr Asn Trp Pro Ile Tyr Ser
                500                 505                 510 cga gaa aaa ctt act agt gca atg ata tgt cat cat ttc agg atg ttc      1584
Arg Glu Lys Leu Thr Ser Ala Met Ile Cys His His Phe Arg Met Phe
                515                 520                 525 aca gca aga gca tgg aac cta act gaa ggt ttc aac gaa tcg atc agc      1632
Thr Ala Arg Ala Trp Asn Leu Thr Glu Gly Phe Asn Glu Ser Ile Ser
```

```
      530             535             540
aac gca gtt gat tac gat atg tat tta aaa ctt agt gaa gtt gga ccg      1680
Asn Ala Val Asp Tyr Asp Met Tyr Leu Lys Leu Ser Glu Val Gly Pro
545                 550                 555                 560 ttc aag cat ata aac aaa att tgt tat aat cgc gta ttg cat ggt gaa      1728
Phe Lys His Ile Asn Lys Ile Cys Tyr Asn Arg Val Leu His Gly Glu
                565                 570                 575 aat acg tct ata aaa aag ttg gat att caa aag gaa aat cat ttt aaa      1776
Asn Thr Ser Ile Lys Lys Leu Asp Ile Gln Lys Glu Asn His Phe Lys
                580                 585                 590 gtt gtt aac gaa tca tta agt agg cta ggc ata aaa aaa tat aaa tat      1824
Val Val Asn Glu Ser Leu Ser Arg Leu Gly Ile Lys Lys Tyr Lys Tyr
                595                 600                 605 tca cca tta act aat ttg aat gaa tgt aga aaa tat acc tgg gaa aaa      1872
Ser Pro Leu Thr Asn Leu Asn Glu Cys Arg Lys Tyr Thr Trp Glu Lys
610                 615                 620 ata gag aat gat tta taa                                              1890
Ile Glu Asn Asp Leu
625

<210> SEQ ID NO 6
<211> LENGTH: 629
<212> TYPE: PRT
<213> ORGANISM: Escherichia coli

<400> SEQUENCE: 6

Lys Ala Val Ile Asp Ile Asp Ala Ala Thr Lys Ile Met Cys Ser Asn
1               5                   10                  15

Ala Lys Ala Ile Ser Leu Asn Glu Val Glu Lys Asn Glu Ile Ile Ser
                20                  25                  30

Lys Tyr Arg Glu Ile Thr Ala Lys Lys Ser Glu Arg Ala Glu Leu Lys
            35                  40                  45

Glu Val Glu Pro Ile Pro Leu Asp Trp Pro Ser Asp Leu Thr Leu Pro
        50                  55                  60

Pro Leu Pro Glu Ser Thr Asn Asp Tyr Val Trp Ala Gly Lys Arg Lys
65                  70                  75                  80

Glu Leu Asp Asp Tyr Pro Arg Lys Gln Leu Ile Ile Asp Gly Leu Ser
                85                  90                  95

Ile Val Ile Pro Thr Tyr Asn Arg Ala Lys Ile Leu Ala Ile Thr Leu
                100                 105                 110

Ala Cys Leu Cys Asn Gln Lys Thr Ile Tyr Asp Tyr Glu Val Ile Val
            115                 120                 125

Ala Asp Asp Gly Ser Lys Glu Asn Ile Glu Glu Ile Val Arg Glu Phe
        130                 135                 140

Glu Ser Leu Leu Asn Ile Lys Tyr Val Arg Gln Lys Asp Tyr Gly Tyr
145                 150                 155                 160

Gln Leu Cys Ala Val Arg Asn Leu Gly Leu Arg Ala Ala Lys Tyr Asn
                165                 170                 175

Tyr Val Ala Ile Leu Asp Cys Asp Met Ala Pro Asn Pro Leu Trp Val
                180                 185                 190

Gln Ser Tyr Met Glu Leu Leu Ala Val Asp Asp Asn Val Ala Leu Ile
            195                 200                 205

Gly Pro Arg Lys Tyr Ile Asp Thr Ser Lys His Thr Tyr Leu Asp Phe
        210                 215                 220

Leu Ser Gln Lys Ser Leu Ile Asn Glu Ile Pro Glu Ile Ile Thr Asn
225                 230                 235                 240

Asn Gln Val Ala Gly Lys Val Glu Gln Asn Lys Ser Val Asp Trp Arg
```

```
                    245                 250                 255
Ile Glu His Phe Lys Asn Thr Asp Asn Leu Arg Leu Cys Asn Thr Pro
                260                 265                 270
Phe Arg Phe Phe Ser Gly Gly Asn Val Ala Phe Ala Lys Lys Trp Leu
            275                 280                 285
Phe Arg Ala Gly Trp Phe Asp Glu Glu Phe Thr His Trp Gly Gly Glu
        290                 295                 300
Asp Asn Glu Phe Gly Tyr Arg Leu Tyr Arg Gly Cys Tyr Phe Arg
305                 310                 315                 320
Ser Val Glu Gly Ala Met Ala Tyr His Gln Glu Pro Pro Gly Lys Glu
                325                 330                 335
Asn Glu Thr Asp Arg Ala Ala Gly Lys Asn Ile Thr Val Gln Leu Leu
            340                 345                 350
Gln Gln Lys Val Pro Tyr Phe Tyr Arg Lys Lys Glu Lys Ile Glu Ser
        355                 360                 365
Ala Thr Leu Lys Arg Val Pro Leu Val Ser Ile Tyr Ile Pro Ala Tyr
    370                 375                 380
Asn Cys Ser Lys Tyr Ile Val Arg Cys Val Glu Ser Ala Leu Asn Gln
385                 390                 395                 400
Thr Ile Thr Asp Leu Glu Val Cys Ile Cys Asp Asp Gly Ser Thr Asp
                405                 410                 415
Asp Thr Leu Arg Ile Leu Gln Glu His Tyr Ala Asn His Pro Arg Val
            420                 425                 430
Arg Phe Ile Ser Gln Lys Asn Lys Gly Ile Gly Ser Ala Ser Asn Thr
        435                 440                 445
Ala Val Arg Leu Cys Arg Gly Phe Tyr Ile Gly Gln Leu Asp Ser Asp
    450                 455                 460
Asp Phe Leu Glu Pro Asp Ala Val Glu Leu Cys Leu Asp Glu Phe Arg
465                 470                 475                 480
Lys Asp Leu Ser Leu Ala Cys Val Tyr Thr Thr Asn Arg Asn Ile Asp
                485                 490                 495
Arg Glu Gly Asn Leu Ile Ser Asn Gly Tyr Asn Trp Pro Ile Tyr Ser
            500                 505                 510
Arg Glu Lys Leu Thr Ser Ala Met Ile Cys His His Phe Arg Met Phe
        515                 520                 525
Thr Ala Arg Ala Trp Asn Leu Thr Glu Gly Phe Asn Glu Ser Ile Ser
    530                 535                 540
Asn Ala Val Asp Tyr Asp Met Tyr Leu Lys Leu Ser Glu Val Gly Pro
545                 550                 555                 560
Phe Lys His Ile Asn Lys Ile Cys Tyr Asn Arg Val Leu His Gly Glu
                565                 570                 575
Asn Thr Ser Ile Lys Lys Leu Asp Ile Gln Lys Glu Asn His Phe Lys
            580                 585                 590
Val Val Asn Glu Ser Leu Ser Arg Leu Gly Ile Lys Lys Tyr Lys Tyr
        595                 600                 605
Ser Pro Leu Thr Asn Leu Asn Glu Cys Arg Lys Tyr Thr Trp Glu Lys
    610                 615                 620
Ile Glu Asn Asp Leu
625

<210> SEQ ID NO 7
<211> LENGTH: 30
<212> TYPE: DNA
<213> ORGANISM: Artificial sequence
<220> FEATURE:
```

```
<223> OTHER INFORMATION: primer

<400> SEQUENCE: 7
cgggatcccg atgagtattc ttaatcaagc                                    30

<210> SEQ ID NO 8
<211> LENGTH: 30
<212> TYPE: DNA
<213> ORGANISM: Artificial sequence
<220> FEATURE:
<223> OTHER INFORMATION: primer

<400> SEQUENCE: 8
ggaattccgg ccagtctaca tgtttatcac                                    30

<210> SEQ ID NO 9
<211> LENGTH: 30
<212> TYPE: DNA
<213> ORGANISM: Artificial sequence
<220> FEATURE:
<223> OTHER INFORMATION: primer

<400> SEQUENCE: 9
cgggatcccg atgagtattc ttaatcaagc                                    30

<210> SEQ ID NO 10
<211> LENGTH: 30
<212> TYPE: DNA
<213> ORGANISM: Artificial sequence
<220> FEATURE:
<223> OTHER INFORMATION: primer

<400> SEQUENCE: 10
ggaattccgg ccagtctaca tgtttatcac                                    30

<210> SEQ ID NO 11
<211> LENGTH: 30
<212> TYPE: DNA
<213> ORGANISM: Artificial sequence
<220> FEATURE:
<223> OTHER INFORMATION: primer

<400> SEQUENCE: 11
gcggccgcaa aacagccaag cttcgaattc                                    30

<210> SEQ ID NO 12
<211> LENGTH: 32
<212> TYPE: DNA
<213> ORGANISM: Artificial sequence
<220> FEATURE:
<223> OTHER INFORMATION: primer

<400> SEQUENCE: 12
acgcgtcgac ggcggatgag agaagatttt ca                                 32

<210> SEQ ID NO 13
<211> LENGTH: 39
<212> TYPE: DNA
<213> ORGANISM: Artificial sequence
<220> FEATURE:
<223> OTHER INFORMATION: primer

<400> SEQUENCE: 13
gcggccgcaa aattaaagag gtatatatta atgtatcga                          39

<210> SEQ ID NO 14
```

```
<211> LENGTH: 24
<212> TYPE: DNA
<213> ORGANISM: Artificial sequence
<220> FEATURE:
<223> OTHER INFORMATION: primer

<400> SEQUENCE: 14
gtcgacctct catccgccaa aaca                                            24

<210> SEQ ID NO 15
<211> LENGTH: 22
<212> TYPE: PRT
<213> ORGANISM: Artificial sequence
<220> FEATURE:
<223> OTHER INFORMATION: partial peptide of KfoA

<400> SEQUENCE: 15

Cys Ile Val Ser Arg Arg Asp Gly Asp Ile Ala Glu Ser Trp Ser Ser
1               5                   10                  15

Pro Glu Lys Ala Asn Lys
            20

<210> SEQ ID NO 16
<211> LENGTH: 17
<212> TYPE: PRT
<213> ORGANISM: Artificial sequence
<220> FEATURE:
<223> OTHER INFORMATION: partial peptide of KfoC

<400> SEQUENCE: 16

Cys Gln Glu Pro Pro Gly Lys Glu Asn Glu Thr Asp Arg Ala Ala Gly
1               5                   10                  15

Lys
```